US009572603B2

(12) United States Patent
Altarac et al.

(10) Patent No.: US 9,572,603 B2
(45) Date of Patent: *Feb. 21, 2017

(54) INTERSPINOUS SPACER

(75) Inventors: Moti Altarac, Irvine, CA (US); Shawn Tebbe, Oceanside, CA (US)

(73) Assignee: VertiFlex, Inc., San Clemente, CA (US)

( * ) Notice: Subject to any disclaimer, the term of this patent is extended or adjusted under 35 U.S.C. 154(b) by 205 days.

This patent is subject to a terminal disclaimer.

(21) Appl. No.: 13/616,547

(22) Filed: Sep. 14, 2012

(65) Prior Publication Data

US 2013/0150886 A1 Jun. 13, 2013

Related U.S. Application Data

(63) Continuation of application No. 12/148,104, filed on Apr. 16, 2008, now Pat. No. 8,292,922, which is a
(Continued)

(51) Int. Cl.
*A61B 17/70* (2006.01)
*A61B 17/00* (2006.01)
*A61F 2/00* (2006.01)

(52) U.S. Cl.
CPC ....... *A61B 17/7067* (2013.01); *A61B 17/7065* (2013.01); *A61B 2017/00004* (2013.01); *A61B 2017/00557* (2013.01); *A61F 2/0077* (2013.01)

(58) Field of Classification Search
CPC ............ A61B 17/7062; A61B 17/7065; A61B 17/7067; A61B 17/7068
(Continued)

(56) References Cited

U.S. PATENT DOCUMENTS 2,248,054 A 7/1941 Becker
2,677,369 A 5/1954 Knowles
(Continued)

FOREIGN PATENT DOCUMENTS

CA 268461 A 2/1927
CN 2794456 Y 7/2006
(Continued)

OTHER PUBLICATIONS

European Search Report Application No. EP05849654.8; Applicant: The Board of Trustees of the Leland Stanford Junior University; Date of Completion: Jun. 21, 2011, 4 pages.
(Continued)

*Primary Examiner* — Pedro Philogene
(74) *Attorney, Agent, or Firm* — Perkins Coie LLP

(57) ABSTRACT

An implantable spacer for placement between adjacent spinous processes in a spinal motion segment is provided. The spacer includes a body defining a longitudinal passageway. A first arm and a second arm are connected to the body. Each arm has a pair of extensions and a saddle defining a U-shaped configuration for seating a spinous process therein. An actuator assembly is disposed inside the longitudinal passageway and connected to the body. When advanced, the actuator assembly contacts camming surfaces of the arms to rotate them from an undeployed configuration to a deployed configuration. In the deployed configuration, the distracted adjacent spinous processes are seated in the U-shaped portion of the arms providing sufficient distraction to open the neural foramen. An insertion instrument is provided for implanting the interspinous process spacer. The system is configured for implantation through a small percutaneous incision employing minimally invasive techniques.

28 Claims, 31 Drawing Sheets

Related U.S. Application Data continuation-in-part of application No. 11/593,995, filed on Nov. 7, 2006, now Pat. No. 8,425,559, which is a continuation-in-part of application No. 11/582,874, filed on Oct. 18, 2006, now Pat. No. 8,128,662, which is a continuation-in-part of application No. 11/314,712, filed on Dec. 20, 2005, now Pat. No. 8,152,837, which is a continuation-in-part of application No. 11/190,496, filed on Jul. 26, 2005, now Pat. No. 8,409,282, which is a continuation-in-part of application No. 11/079,006, filed on Mar. 10, 2005, now Pat. No. 8,012,207, which is a continuation-in-part of application No. 11/052,002, filed on Feb. 4, 2005, now Pat. No. 8,317,864, which is a continuation-in-part of application No. 11/006,502, filed on Dec. 6, 2004, now Pat. No. 8,123,807, which is a continuation-in-part of application No. 10/970,843, filed on Oct. 20, 2004, now Pat. No. 8,167,944.

(60) Provisional application No. 60/923,971, filed on Apr. 17, 2007, provisional application No. 60/923,841, filed on Apr. 16, 2007.

(58) Field of Classification Search
USPC ............... 606/246–279; 623/17.11–17.16
See application file for complete search history.

(56) References Cited

U.S. PATENT DOCUMENTS

| | | |
|---|---|---|
| 3,242,120 A | 3/1966 | Steuber |
| 3,486,505 A | 12/1969 | Morrison |
| 3,648,691 A | 3/1972 | Lumb et al. |
| 3,986,383 A | 10/1976 | Petteys |
| 4,545,374 A | 10/1985 | Jacobson |
| 4,632,101 A | 12/1986 | Freedland |
| 4,685,447 A | 8/1987 | Iversen et al. |
| 4,799,484 A | 1/1989 | Smith et al. |
| 4,863,476 A | 9/1989 | Shepperd |
| 4,895,564 A | 1/1990 | Farrell |
| 4,986,831 A | 1/1991 | King et al. |
| 5,011,484 A | 4/1991 | Breard et al. |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |

(56) References Cited

U.S. PATENT DOCUMENTS

| | | |
|---|---|---|
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,245 B2 | 4/2004 | Pasquet et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |

(56) References Cited

U.S. PATENT DOCUMENTS

| | | |
|---|---|---|
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 * | 10/2012 | Altarac .......................... 606/249 |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 2001/0031965 A1 | 10/2001 | Zucherman et al. |
| 2002/0143331 A1 | 10/2002 | Zucherman et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markwort |
| 2004/0087947 A1 | 5/2004 | Lim et al. |
| 2004/0106997 A1 | 6/2004 | Lieberson |
| 2004/0106999 A1 | 6/2004 | Mathews |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0261768 A1 | 11/2005 | Trieu |
| 2005/0278036 A1 | 12/2005 | Leonard et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 * | 4/2006 | Kim .................. A61B 17/7065 606/249 |
| 2006/0084991 A1 | 4/2006 | Borgstrom et al. |
| 2006/0085069 A1 | 4/2006 | Kim |
| 2006/0085070 A1 * | 4/2006 | Kim .................. A61B 17/7065 623/17.11 |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 * | 11/2006 | Zucherman et al. ....... 623/17.11 |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191948 A1 | 8/2007 | Arnin et al. |
| 2007/0191991 A1 * | 8/2007 | Addink .................. A01G 25/16 700/284 |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |

(56) References Cited

U.S. PATENT DOCUMENTS

| | | |
|---|---|---|
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Solsberg et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0086212 A1 | 4/2008 | Zucherman et al. |
| 2008/0108990 A1* | 5/2008 | Mitchell et al. ............... 606/61 |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1* | 7/2008 | Lamborne ......... A61B 17/7065 606/246 |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1* | 1/2009 | Aschmann ......... A61B 17/7065 606/99 |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1* | 5/2009 | Altarac et al. ............... 606/249 |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1* | 5/2010 | Roebling et al. ............. 606/249 |
| 2010/0228092 A1 | 9/2010 | Ortiz et al. |
| 2010/0234889 A1* | 9/2010 | Hess ........................ 606/249 |
| 2010/0262243 A1 | 10/2010 | Zucherman et al. |
| 2010/0280551 A1* | 11/2010 | Pool et al. .................... 606/249 |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1* | 3/2012 | Hess ........................ 606/248 |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0228884 A1 | 8/2014 | Altarac et al. |
| 2014/0275992 A1 | 9/2014 | Choi et al. |
| 2015/0150598 A1 | 6/2015 | Tebbe et al. |
| 2015/0150604 A1 | 6/2015 | Kim |
| 2015/0164560 A1 | 6/2015 | Altarac et al. |
| 2015/0374415 A1 | 12/2015 | Kim |
| 2016/0030092 A1 | 2/2016 | Altarac et al. |
| 2016/0045232 A1 | 2/2016 | Altarac et al. |

(56) References Cited

U.S. PATENT DOCUMENTS

| | | |
|---|---|---|
| 2016/0066963 A1 | 3/2016 | Kim |
| 2016/0135853 A1 | 5/2016 | Altarac et al. |
| 2016/0248222 A1 | 8/2016 | Miyata |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-2004073533 A1 | 9/2004 |
| WO | WO-2004110300 A2 | 12/2004 |
| WO | WO-2005009300 A1 | 2/2005 |
| WO | WO-2005013839 A2 | 2/2005 |
| WO | WO-2005025461 A2 | 3/2005 |
| WO | WO-2005041799 A1 | 5/2005 |
| WO | WO-2005044152 A1 | 5/2005 |
| WO | WO-2005055868 A2 | 6/2005 |
| WO | WO-2005079672 A2 | 9/2005 |
| WO | WO-2005086776 A2 | 9/2005 |
| WO | WO-2005115261 A1 | 12/2005 |
| WO | WO-2006033659 A2 | 3/2006 |
| WO | WO-2006034423 A2 | 3/2006 |
| WO | WO-2006039243 | 4/2006 |
| WO | WO-2006039260 A2 | 4/2006 |
| WO | WO-2006045094 A2 | 4/2006 |
| WO | WO-2006063047 A2 | 6/2006 |
| WO | WO-2006064356 A1 | 6/2006 |
| WO | WO-2006065774 A1 | 6/2006 |
| WO | WO-2006089085 A2 | 8/2006 |
| WO | WO-2006102269 A2 | 9/2006 |
| WO | WO-2006102428 A1 | 9/2006 |
| WO | WO-2006102485 A2 | 9/2006 |
| WO | WO-2006107539 A1 | 10/2006 |
| WO | WO-2006110462 A2 | 10/2006 |
| WO | WO-2006110464 A1 | 10/2006 |
| WO | WO-2006110767 A1 | 10/2006 |
| WO | WO-2006113080 A2 | 10/2006 |
| WO | WO-2006113406 A2 | 10/2006 |
| WO | WO-2006113814 A2 | 10/2006 |
| WO | WO-2006118945 A1 | 11/2006 |
| WO | WO-2006119235 A1 | 11/2006 |
| WO | WO-2006119236 A2 | 11/2006 |
| WO | WO-2006135511 A1 | 12/2006 |
| WO | WO-2007015028 A1 | 2/2007 |
| WO | WO-2007035120 A1 | 3/2007 |
| WO | WO-2007075375 A2 | 7/2007 |
| WO | WO-2007075788 A2 | 7/2007 |
| WO | WO-2007075791 A2 | 7/2007 |
| WO | WO-2007089605 A2 | 8/2007 |
| WO | WO-2007089905 A2 | 8/2007 |
| WO | WO-2007089975 A1 | 8/2007 |
| WO | WO-2007097735 A2 | 8/2007 |
| WO | WO-2007109402 A2 | 9/2007 |
| WO | WO-2007110604 A1 | 10/2007 |
| WO | WO-2007111795 A1 | 10/2007 |
| WO | WO-2007111979 A2 | 10/2007 |
| WO | WO-2007111999 A2 | 10/2007 |
| WO | WO-2007117882 A1 | 10/2007 |
| WO | WO-2007121070 A2 | 10/2007 |
| WO | WO-2007127550 A2 | 11/2007 |
| WO | WO-2007127588 A1 | 11/2007 |
| WO | WO-2007127677 A1 | 11/2007 |
| WO | WO-2007127689 A2 | 11/2007 |
| WO | WO-2007127694 A2 | 11/2007 |
| WO | WO-2007127734 A2 | 11/2007 |
| WO | WO-2007127736 A2 | 11/2007 |
| WO | WO-2007131165 A2 | 11/2007 |
| WO | WO-2007134113 A2 | 11/2007 |
| WO | WO-2008009049 A1 | 1/2008 |
| WO | WO-2008048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

International Search Report and Written Opinion; Application No. PCT/US2005/038026; Mailing Date: Apr. 22, 2008, 9 pages.
International Search Report and Written Opinion; Application No. PCT/US2005/044256; Mailing Date: Jul. 28, 2006, 7 pages.
International Search Report and Written Opinion; Application No. PCT/US2006/047824; Mailing Date: Oct. 16, 2008, 17 pages.
International Search Report and Written Opinion; Application No. PCT/US2006/048611; Mailing Date: Oct. 14, 2008; 10 pages.
International Search Report and Written Opinion; Application No. PCT/US2006/048614; Mailing Date: Feb. 3, 2006; 23 pages.
International Search Report and Written Opinion; Application No. PCT/US2007/022171; Mailing Date: Apr. 15, 2008, 9 pages.
International Search Report and Written Opinion; Application No. PCT/US2007/023312; Mailing Date: May 22, 2008, 14 pages.
International Search Report and Written Opinion; Application No. PCT/US2008/004901; Mailing Date: Aug. 19, 2008, 7 pages.
International Search Report and Written Opinion; Application No. PCT/US2008/008382; Mailing Date: Mar. 2, 2009, 13 pages.

(56) References Cited

OTHER PUBLICATIONS

International Search Report and Written Opinion; Application No. PCT/US2008/008983; Mailing Date: Feb. 23, 2009, 7 pages.
International Search Report and Written Opinion; Application No. PCT/US2008/087527; Mailing Date: Jul. 30, 2009, 10 pages.
International Search Report and Written Opinion; Application No. PCT/US2009/031150; Mailing Date: Aug. 28, 2009, 6 pages.
International Search Report and Written Opinion; Application No. PCT/US2009/031710; Mailing Date: Sep. 1, 2009, 10 pages.
International Search Report and Written Opinion; Application No. PCT/US2009/036561; Mailing Date: Sep. 17, 2009, 12 pages.
Minns, R.J., et al., "Preliminary Design and Experimental Studies of a Novel Soft Implant for Correcting Sagittal Plane Instability in the Lumbar Spine," (1997) Spine, 22(16): 1819-1827.
Supplementary European Search Report; Application No. EP05849654.6; Applicant: Vertiflex, Inc.; Date of Completion: May 15, 2009, 10 pages.
Supplementary European Search Report; Application No. EP07861426.0; Applicant: Vertiflex, Inc.; Date of Completion: Jun. 7, 2011, 6 pages.
Supplementary European Search Report; Application No. EP07861721.4; Applicant: Vertiflex, Inc.; Date of Completion: Nov. 24, 2009, 6 pages.
Supplementary European Search Report; Application No. EP09170304.1; Applicant: Vertiflex, Inc.; Date of Completion: Nov. 11, 2009, 5 pages.
Supplementary European Search Report; Application No. EP09170338.9; Applicant: Vertiflex, Inc.; Date of Completion: Nov. 12, 2009, 6 pages.
Supplementary European Search Report; Application No. EP09702116.6; Applicant: Vertiflex, Inc.; Date of Completion: Feb. 11, 2011, 6 pages.
Supplementary European Search Report; Application No. EP11151901.3; Applicant: Vertiflex, Inc.; Date of Completion: Apr. 7, 2011, 6 pages.
Swan, Colby, "Preliminary Design and Experimental Studies of a Novel Soft Implant for Correcting Sogittal Plane Instability in the Lumbar Spine," Spine, 1997, 22(16), 1826-1827.
Supplementary European Search Report; Application No. EP05815519.3; Applicant: The Board of Trustees of Leland Stanford Junior University; Date of Completion: Sep. 28, 2011, 9 pages.
Supplementary European Search Report; Application No. EP05849654; Applicant: The Board of Trustees of Leland Stanford Junior University; Date of Completion: May 15, 2009, 5 pages.
Australia Exam Report for Application No. AU2006329867, Applicant: The Board of Trustees of Leland Stanford Junior University; Date of Issue: Jan. 27, 2012, 2 pages.
Australia Exam Report for Application No. AU2007317886, Applicant: VertiFlex, Inc.; Date of Issue: Jun. 18, 2012, 3 pages.
Australia Exam Report for Application No. AU2008241447, Applicant: VertiFlex, Inc.; Date of Issue: Jul. 5, 2012, 4 pages.
Australia Exam Report for Application No. AU2008275708, Applicant: VertiFlex, Inc.; Date of Issue: Nov. 12, 2012, 4 pages.
Australia Exam Report for Application No. AU2008296066, Applicant: VertiFlex, Inc.; Date of Issue: Mar. 6, 2013, 3 pages.
Australia Exam Report for Application No. AU2008343092, Applicant: VertiFlex, Inc.; Date of Issue: Feb. 8, 2013, 4 pages.
Australia Exam Report No. 2 for Application No. AU2009206098, Applicant: VertiFlex, Inc.; Date of Issue: Aug. 19, 2014, 4 pages.
Australia Exam Report No. 1 for Application No. AU2009206098, Applicant: VertiFlex, Inc.; Date of Issue: Mar. 6, 2013, 4 pages.
Canada Exam Report for Application No. CA2634251, Applicant: The Board of Trustees of Leland Stanford Junior University; Date of Issue: Dec. 3, 2013, 2 pages.
Canada Exam Report for Application No. CA2668833, Applicant: Vertiflex, Inc.; Date of Issue: Dec. 5, 2013, 2 pages.
Canada Exam Report for Application No. CA2695937, Applicant: Vertiflex, Inc.; Date of Issue: Aug. 7, 2014, 2 pages.
Canada Exam Report for Application No. CA2697628, Applicant: Vertiflex, Inc.; Date of Issue: Oct. 16, 2014, 2 pages.
Canada Exam Report for Application No. CA2698718, Applicant: Vertiflex, Inc.; Date of Issue: May 20, 2014, 3 pages.
Supplementary European Search Report; Application No. EP06845480; Applicant: VertiFlex, Inc.; Date of Completion: Aug. 14, 2012, 9 pages.
Supplementary European Search Report for Application No. EP13184922.6; Applicant: VertiFlex, Inc.; Date of Issue: Oct. 30, 2013, 8 pages.
Supplementary European Search Report for Application No. EP07861426; Applicant: VertiFlex, Inc.; Date of Issue: Jun. 7, 2011, 6 pages.
Supplementary European Search Report for Application No. EP07861721.4; Applicant: VertiFlex, Inc.; Date of Issue: Nov. 24, 2009, 6 pages.
Supplementary European Search Report for Application No. EP09170304.1; Applicant: VertiFlex, Inc.; Date of Issue: Nov. 24, 2009, 5 pages.
Supplementary European Search Report for Application No. EP09170338.9; Applicant: VertiFlex, Inc.; Date of Issue: Nov. 24, 2009, 6 pages.
Supplementary European Search Report for Application No. EP11151901.3; Applicant: VertiFlex, Inc.; Date of Issue: Apr. 7, 2011, 6 pages.
Supplementary European Search Report for Application No. EP08742949.4; Applicant: VertiFlex, Inc.; Date of Issue: Sep. 17, 2012, 6 pages.
Supplementary European Search Report for Application No. EP08780034.8; Applicant: VertiFlex, Inc.; Date of Issue: Sep. 19, 2012, 7 pages.
Supplementary European Search Report for Application No. EP08794704.0; Applicant: VertiFlex, Inc.; Date of Issue: Oct. 23, 2012, 9 pages.
Supplementary European Search Report for Application No. EP08799267.3; Applicant: VertiFlex, Inc.; Date of Issue: Jun. 29, 2011, 7 pages.
Supplementary European Search Report for Application No. EP08867282.9; Applicant: VertiFlex, Inc.; Date of Issue: Nov. 28, 2012, 10 pages.
Supplementary European Search Report for Application No. EP09702116.6; Applicant: VertiFlex, Inc.; Date of Issue: Feb. 11, 2011, 7 pages.
International Search Report and Written Opinion; Application No. PCT/US2010/060498; Mailing Date: Aug. 25, 2011, 17 pages.
Australia Exam Report for Application No. AU2009223607, Applicant: VertiFlex, Inc.; Date of Issue: Jun. 4, 2013, 3 pages.
International Search Report, counterpart PCT Application PCT/US2013/038534, Applicant: Vertiflex, Inc., Aug. 7, 2013, 16 pages.
McCulloch, John A., Young, Paul H., "Essentials of Spinal Microsurgery," 1998, pp. 453-485. Lippincott-Raven Publishers, Philadelphia, PA (37 pages total).
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
Vertos mild Devices Kit—PRT-00430-C—Instructions for Use (13 pages total); see http://vertosmed.com/docs/mildIFU_PRT-00430-C.pdf., 2012.
Decision on Petition in U.S. Appl. No. 60/592,099, May 4, 2005.
Vaccaro, Alexander J. et al., MasterCases Spine Surgery, 2001, pp. 100-107. Thieme Medical Publishers, Inc., NY. (10 pages total).
Tredway, Trent L. et al., "Minimally Invasive Transforaminal Lumbar Interbody Fusion (MI-TLIF) and Lateral Mass Fusion with the MetRx System," (14 pages total), 2005.
Fast, Avital et al., "Surgical Treatment of Lumbar Spinal Stenosis in the Elderly," Arch Phys. Med Rehabil., Mar. 1985, pp. 149-151, vol. 66.

(56) References Cited

OTHER PUBLICATIONS

Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
International Search Report and Written Opinion; Application No. PCT/US2009/029537; Applicant: Vertiflex, Inc. Mailing Date: Aug. 3, 2015, 14 pages.
ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
Australia Exam Report for Application No. AU2014203394, Applicant: VertiFlex, Inc., Date of Issue: Mar. 15, 2016, 2 pages.
European Further Exam Report for Application No. EP09702116.6; Applicant: VertiFlex, Inc.; Date of Mailing: Jul. 4, 2016, 4 pages.

\* cited by examiner

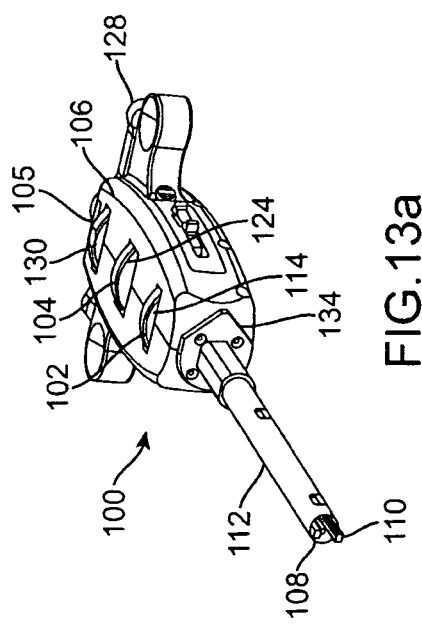
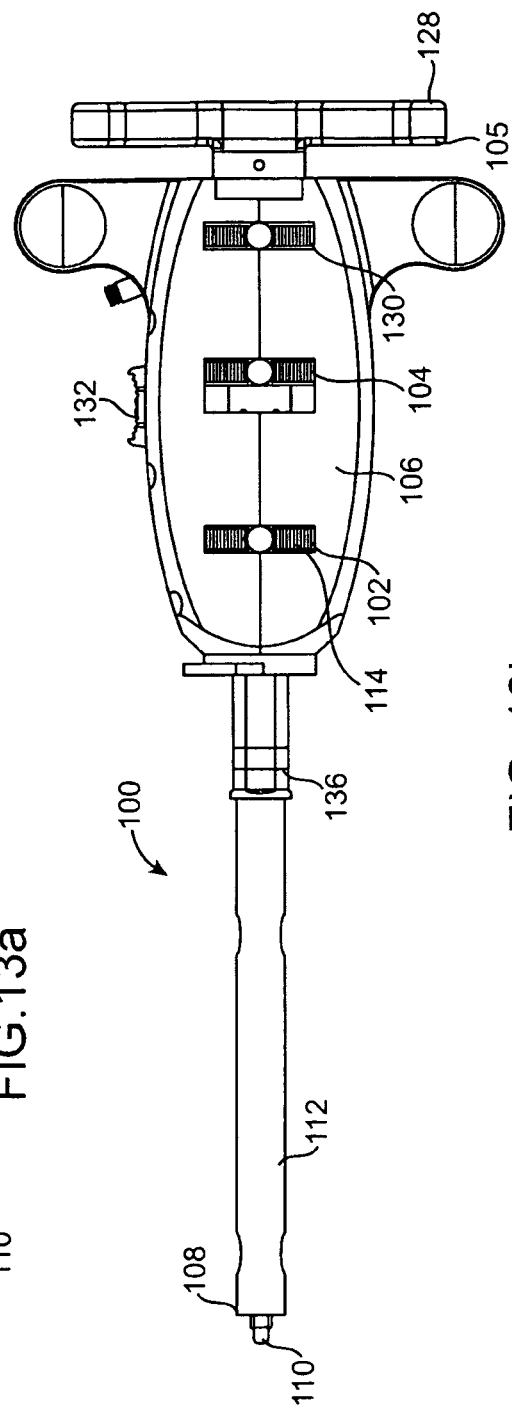
FIG. 13a
FIG. 13b

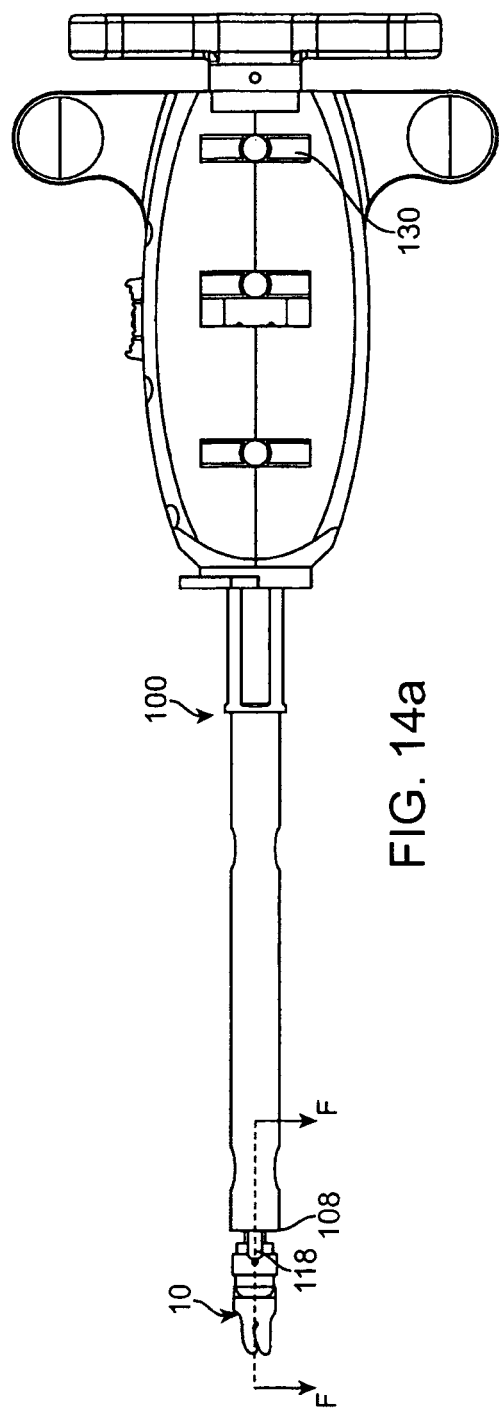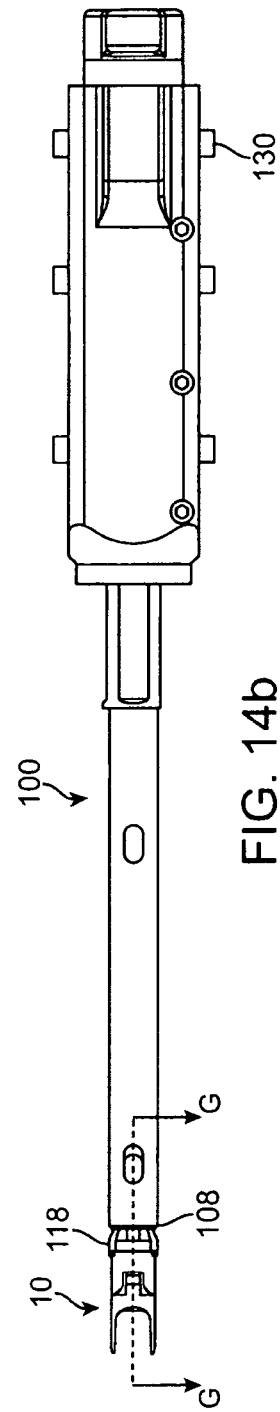

SECTION G-G

SECTION F-F

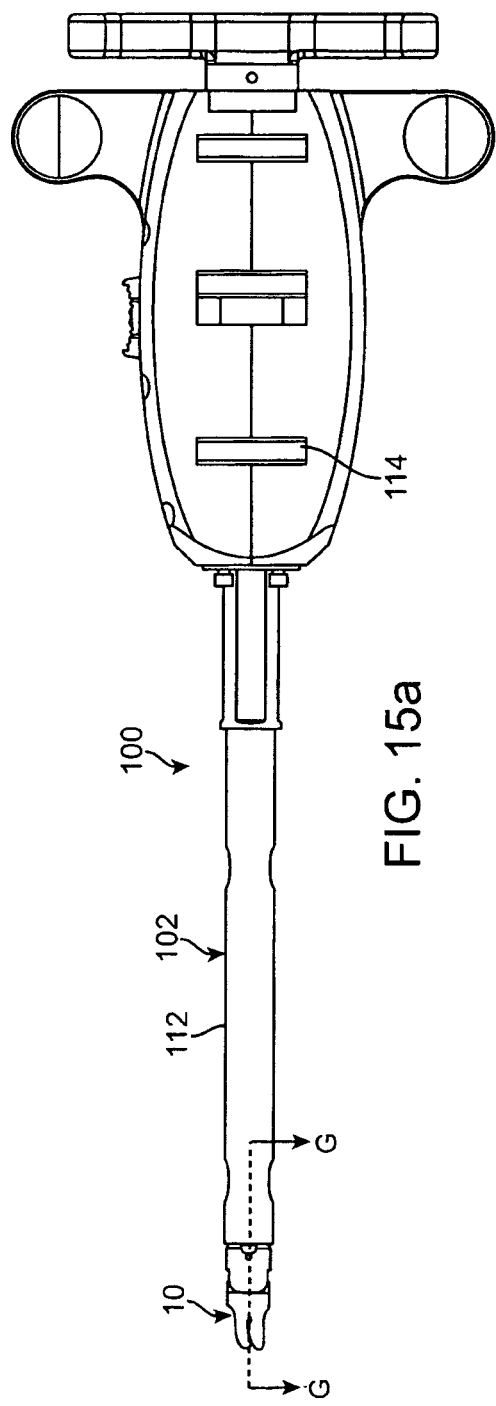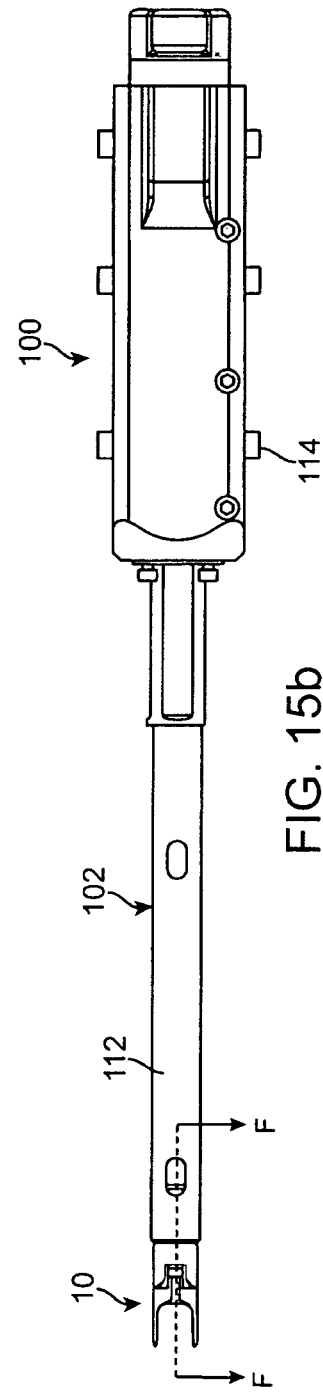

SECTION G-G

SECTION F-F

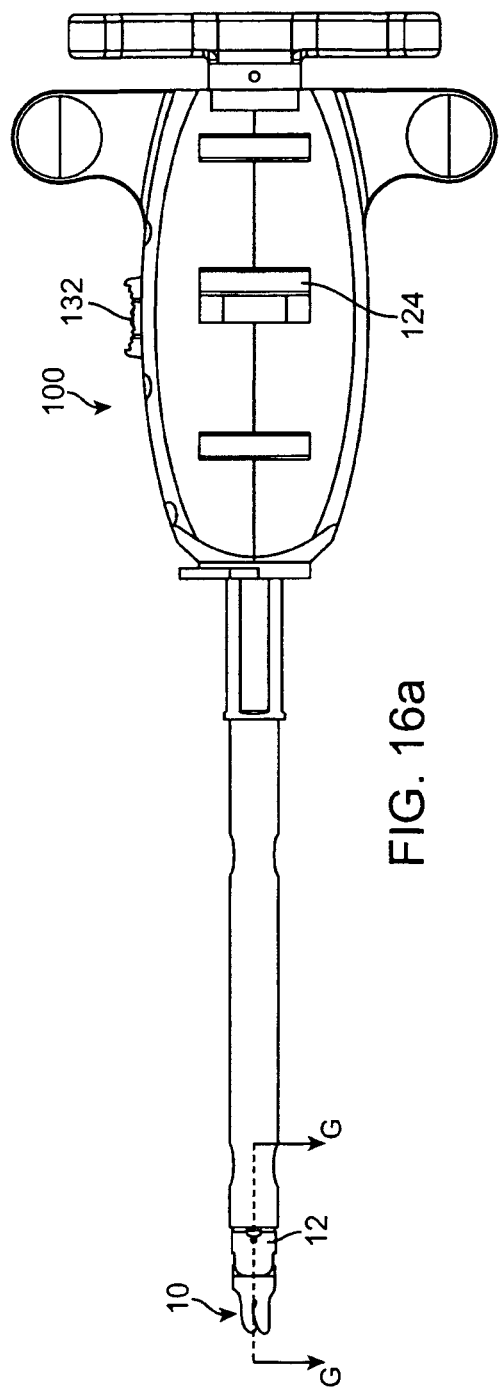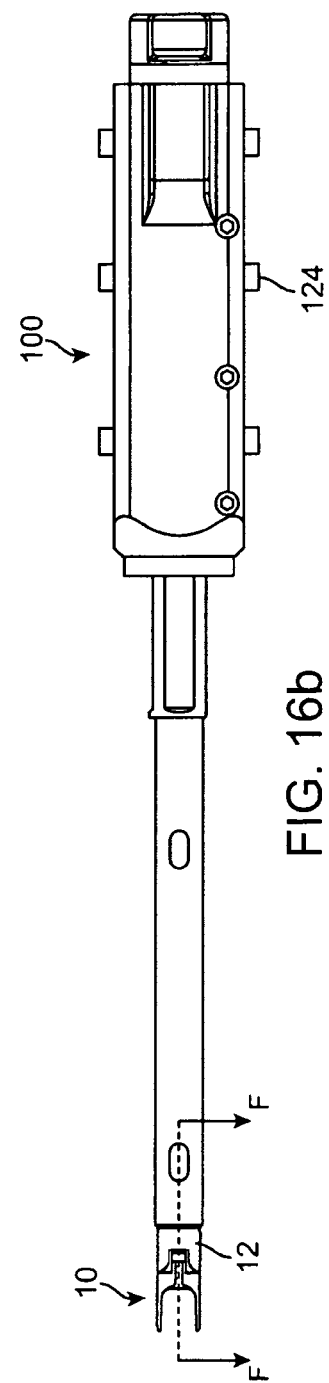

SECTION F-F

SECTION G-G

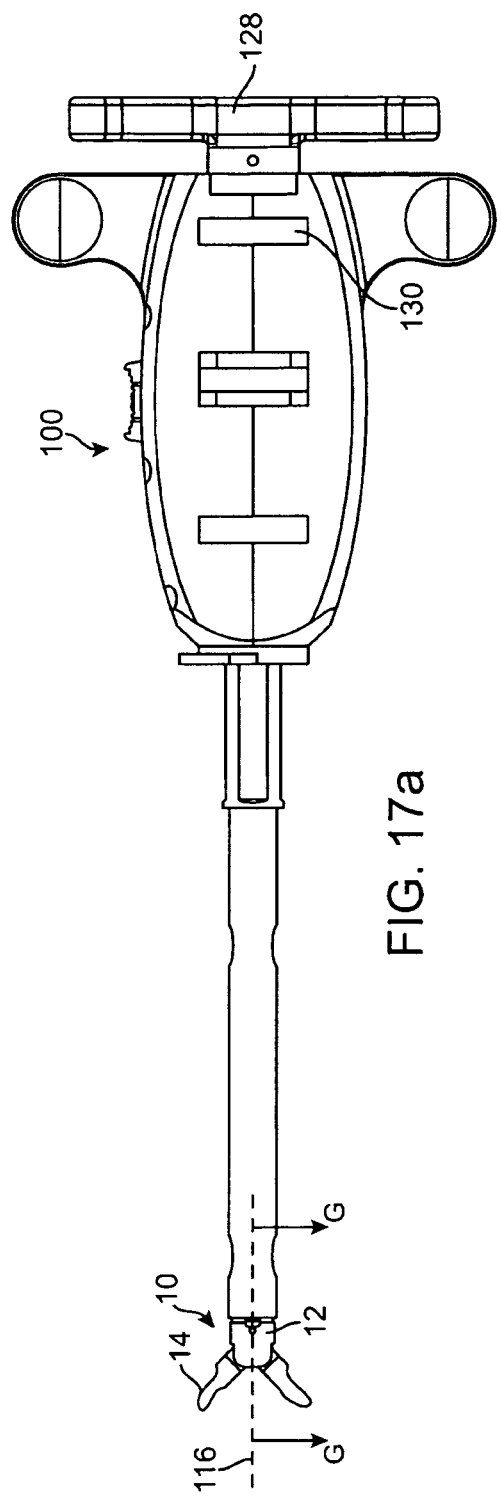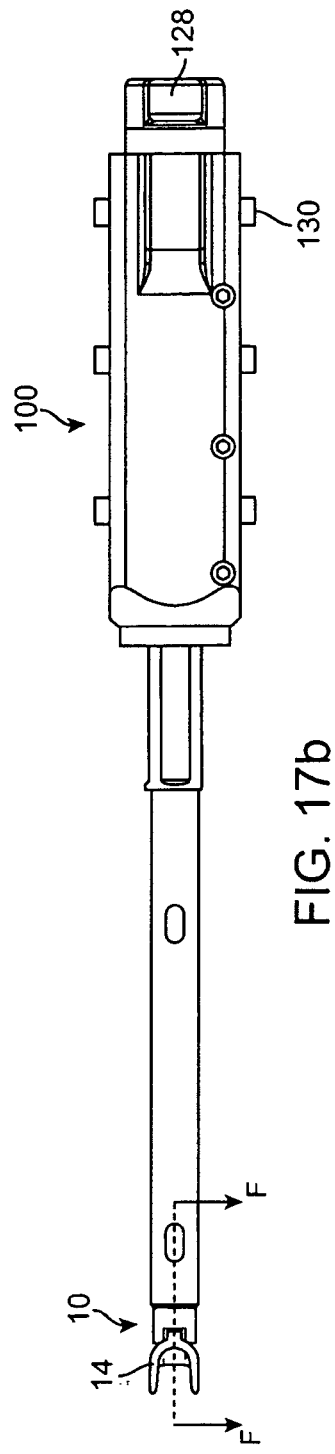

SECTION F-F

SECTION G-G

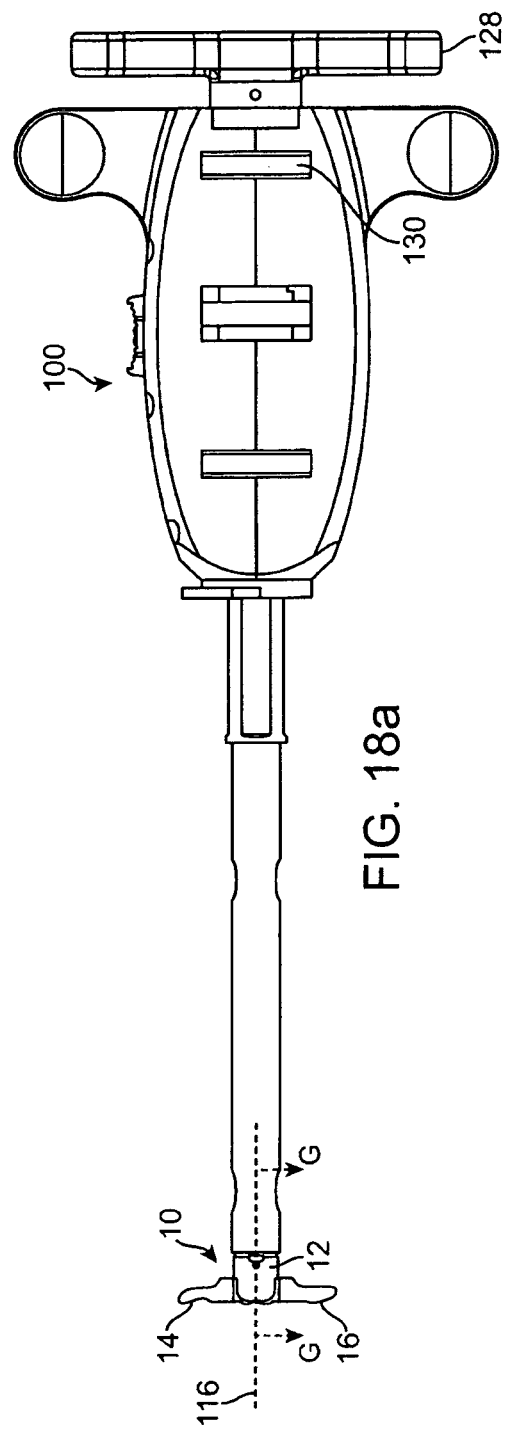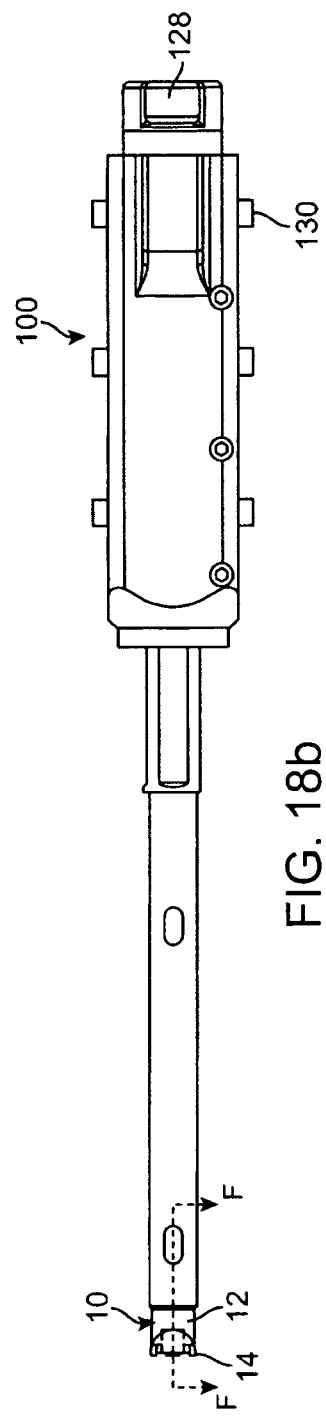
FIG. 18a
FIG. 18b

SECTION F-F

SECTION G-G

INTERSPINOUS SPACER

CROSS-REFERENCE TO RELATED APPLICATIONS

This application claims the benefit of U.S. Provisional Patent Application Ser. No. 60/923,971 entitled "Interspinous spacer" filed on Apr. 17, 2007 and U.S. Provisional Patent Application Ser. No. 60/923,841 entitled "Spacer insertion instrument" filed on Apr. 16, 2007, each of which is hereby incorporated by reference in its entirety. This application is also a continuation of U.S. patent application Ser. No. 12/148,104 entitled "Interspinous Spacer" filed on Apr. 16, 2008 which is a continuation-in-part of U.S. patent application Ser. No. 11/593,995 entitled "Systems and methods for posterior dynamic stabilization of the spine" filed on Nov. 7, 2006 which is a continuation-in-part of U.S. patent application Ser. No. 11/582,874 entitled "Minimally invasive tooling for delivery of interspinous spacer" filed on Oct. 18, 2006, now U.S. Pat. No. 8,128,662, which is a continuation-in-part of U.S. patent application Ser. No. 11/314,712 entitled "Systems and methods for posterior dynamic stabilization of the spine" filed on Dec. 20, 2005, now U.S. Pat. No. 8,152,837, which is a continuation-in-part of U.S. patent application Ser. No. 11/190,496 entitled "Systems and methods for posterior dynamic stabilization of the spine" filed on Jul. 16, 2005 which is a continuation-in-part of U.S. patent application Ser. No. 11/079,006 entitled "Systems and methods for posterior dynamic stabilization of the spine" filed on Mar. 10, 2005, now U.S. Pat. No. 8,012,207, which is a continuation-in-part of U.S. patent application Ser. No. 11/052,002 entitled "Systems and methods for posterior dynamic stabilization of the spine" filed on Feb. 4, 2005 which is a continuation-in-part of U.S. patent application Ser. No. 11/006,502 entitled "Systems and methods for posterior dynamic stabilization of the spine" filed on Dec. 6, 2004, now U.S. Pat. No. 8,123,807, which is a continuation-in-part of U.S. patent application Ser. No. 10/970,843 entitled "Systems and methods for posterior dynamic stabilization of the spine" filed on Oct. 20, 2004, now U.S. Pat. No. 8,167,944, all of which are hereby incorporated by reference in their entireties.

FIELD

The present invention generally relates to medical devices, in particular, implants for placement between adjacent interspinous processes of a patient's spine.

BACKGROUND

With spinal stenosis, the spinal canal narrows and pinches the spinal cord and nerves, causing pain in the back and legs. Typically, with age, a person's ligaments may thicken, intervertebral discs may deteriorate and facet joints may break down—all contributing to the condition of the spine characterized by a narrowing of the spinal canal. Injury, heredity, arthritis, changes in blood flow and other causes may also contribute to spinal stenosis.

Doctors have been at the forefront with various treatments of the spine including medications, surgical techniques and implantable devices that alleviate and substantially reduce debilitating pain associated with the back. In one surgical technique, a spacer is implanted between adjacent interspinous processes of a patient's spine. The implanted spacer opens the spinal canal, maintains the desired distance between vertebral body segments, increases the neural foramen space and as a result, avoids impingement of nerves and relieves pain. For suitable candidates, an implantable interspinous spacer may provide significant benefits in terms of pain relief.

Any surgery is an ordeal. However, the type of device and how it is implanted has an impact. For example, one consideration when performing surgery to implant an interspinous spacer is the size of the incision that is required to allow introduction of the device. Small incisions and minimally invasive techniques are generally preferred as they affect less tissue and result in speedier recovery times. As such, there is a need for interspinous spacers that work well with surgical techniques that are minimally invasive for the patient. The present invention sets forth such a spacer and associated instrumentation.

SUMMARY

According to one aspect of the invention, an implantable spacer for placement between adjacent interspinous processes in a spinal motion segment is disclosed. The spacer includes a body defining a longitudinal passageway and a longitudinal axis. The spacer further includes a first arm and a second arm connected to the body and capable of rotation with respect to the body. Each arm has a pair of extensions and configured for containing a spinous process therein. Each arm has a proximal camming surface. The spacer further includes an actuator assembly connected to the body. The actuator assembly includes an actuator having a proximal end and a distal end. The actuator has at least one bearing surface at the distal end that is configured to engage each camming surface. The actuator is connected to the body and configured to move inside the longitudinal passageway relative to the body to contact each camming surface with the at least one bearing surface and thereby move the arms from an undeployed configuration in which the arms are substantially parallel to the longitudinal axis of the body to a deployed configuration in which the arms are substantially perpendicular to the longitudinal axis of the body to contain adjacent spinous processes when in the deployed configuration.

According to another aspect of the invention, an insertion instrument configured for delivering a spacer to an interspinous process space of a patient and deploying the spacer from an undeployed configuration to at least one deployed configuration to relieve pain is disclosed. The spacer includes a body, at least one arm connected to and movable with respect to the body and a spacer actuator having a proximal end and a distal end disposed at least partially inside the body. The spacer actuator is configured to move the at least one arm from an undeployed configuration to at least one deployed configuration. The insertion instrument includes a handle assembly, a first assembly connected to the handle assembly, a second assembly connected to the handle assembly and a third assembly connected to the handle assembly. The first assembly is configured to connect to the body of the spacer at the distal end of the insertion instrument. The first assembly has a first control at the handle assembly configured to connect and release the body of the spacer and the first assembly. The second assembly is configured to connect to the proximal end of the actuator of the spacer at the distal end of the insertion instrument. The second assembly has a second control at the handle assembly configured to connect and release the actuator and the second assembly. The third assembly is configured to move the second assembly relative to the body of the spacer for arranging the spacer from an undeployed configuration to at least one deployed configuration.

According to another aspect of the invention, a method for implanting a spacer between a superior spinous process and an adjacent inferior spinous process of a patient's spine is disclosed. The method includes the step of providing a spacer. The spacer includes a body having a proximal end, a distal end, and a longitudinal axis. The spacer also includes a first arm and a second arm connected to the body at the distal end. The first and second arms are configured to contain the superior and inferior spinous processes. The spacer further includes an actuator configured to move the first and second arms from a low-profile undeployed configuration in which the first and second arms extend parallel to longitudinal axis to at least one deployed configuration in which the first and second arms are transverse to the longitudinal axis. The method includes the step of inserting the spacer into an interspinous process space from the posterior side of the patient and may be inserted through the superspinous ligament while in the undeployed configuration. The method includes the step of arranging the spacer into at least one deployed configuration.

Other advantages will be apparent from the description that follows, including the drawings and claims.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 13a illustrates a perspective view of a spacer insertion instrument according to the present invention.

FIG. 13b illustrates a side view of a spacer insertion instrument according to the present invention.

FIG. 14a illustrates side view of a spacer insertion instrument in juxtaposition to a spacer according to the present invention.

FIG. 14b illustrates a top view of a spacer insertion instrument in juxtaposition to a spacer according to the present invention.

FIG. 15a illustrates a side view of a spacer insertion instrument connected to a spacer according to the present invention.

FIG. 15b illustrates a top view of a spacer insertion instrument connected to a spacer according to the present invention.

FIG. 16a illustrates a side view of a spacer insertion instrument connected to a spacer according to the present invention.

FIG. 16b illustrates a top view of a spacer insertion instrument connected to a spacer according to the present invention.

FIG. 17a illustrates a side view of a spacer insertion instrument connected to a spacer in a partially deployed configuration according to the present invention.

FIG. 17b illustrates a top view of a spacer insertion instrument connected to a spacer in a partially deployed configuration according to the present invention.

FIG. 18a illustrates a side view of a spacer insertion instrument connected to a spacer in a deployed configuration according to the present invention.

FIG. 18b illustrates a top view of a spacer insertion instrument connected to a spacer in a deployed configuration according to the present invention.

DETAILED DESCRIPTION

Figure 1A:
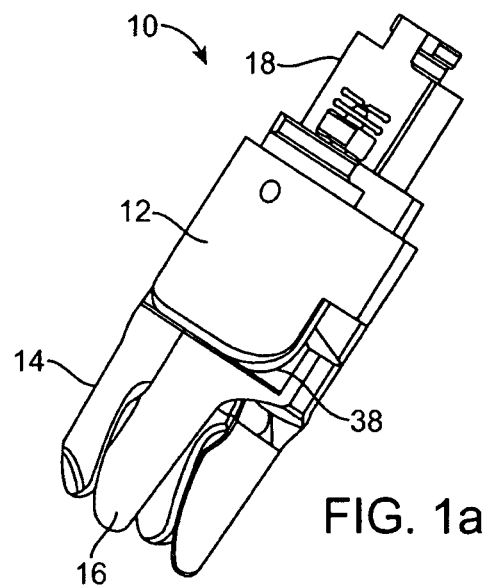
FIG. 1a illustrates a perspective view of a spacer according to the present invention.
Figure 1B:
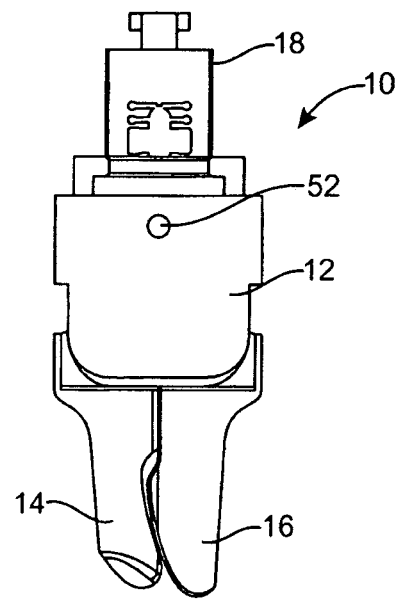
FIG. 1b illustrates a side view of a spacer according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention is described in the accompanying figures and text as understood by a person having ordinary skill in the field of spinal implants and implant delivery instrumentation.

With reference to FIGS. 1a-1e, various views of a spacer 10 according to the present invention are shown. The spacer 10 includes a body 12 connected to a superior extension member or arm 14, an inferior extension member or arm 16, and an actuator assembly 18.

Turning now to FIGS. 2a-2d, the body 12 will now be described. The body 12 is shown to have a clamshell construction with a left body piece 20 (shown in FIGS. 2a and 2b) joined to a right body piece 22 (shown in FIGS. 2c and 2d) to capture arms 14, 16 inside. With the right and left body pieces 20, 22 joined together, the body 12 is generally cylindrical. It has a cross-sectional size and shape that allows for implantation between adjacent spinous processes and facilitates delivery into a patient through a narrow port or cannula.

The inside of the body 12 defines an arm receiving portion 24 and an actuator assembly receiving portion 26 with features formed in each of the left and right body pieces 20, 22 that together define the arm and actuator assembly receiving portions 24, 26. In one variation, the arm receiving portion 24 includes slots 28 that receive pins formed on the arms 14, 16 such that the pins rotate and/or translate inside the slots 28. The actuator assembly receiving portion 26 includes a passageway 30. Other features include a tongue 31a and groove 31b for mating with the opposite clamshell.

Figure 1C:
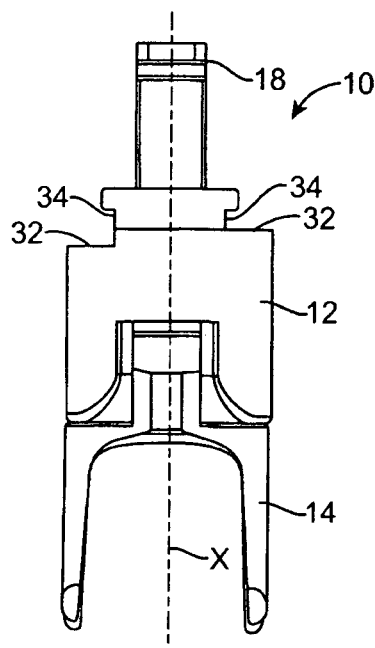
FIG. 1c illustrates a top view of a spacer according to the present invention.
Figure 1D:
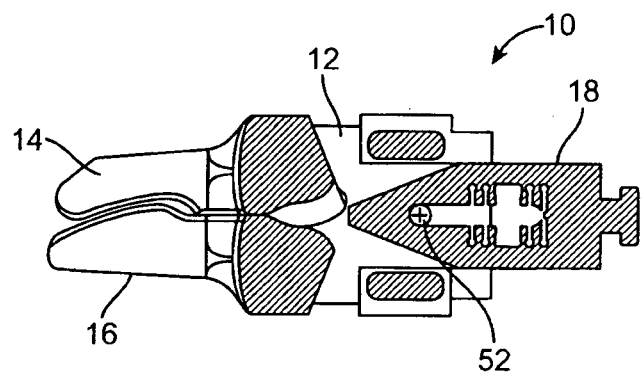
FIG. 1d illustrates a cross-sectional view of the spacer of FIG. 1c taken along line X according to the present invention.
Figure 1E:
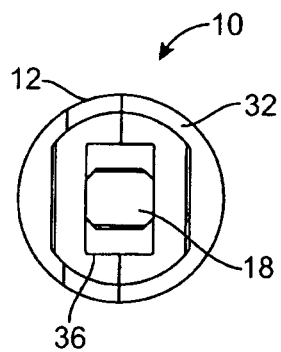
FIG. 1e illustrates an end view of a spacer according to the present invention.
Figure 2A:
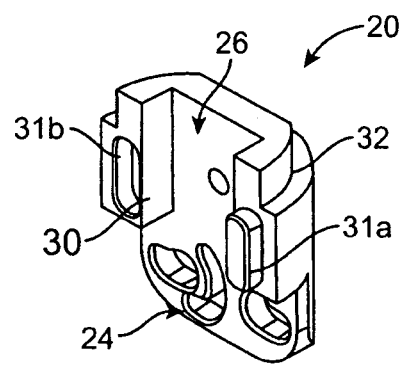
FIG. 2a illustrates a perspective view of half of a body of a spacer according to the present invention.
Figure 2B:
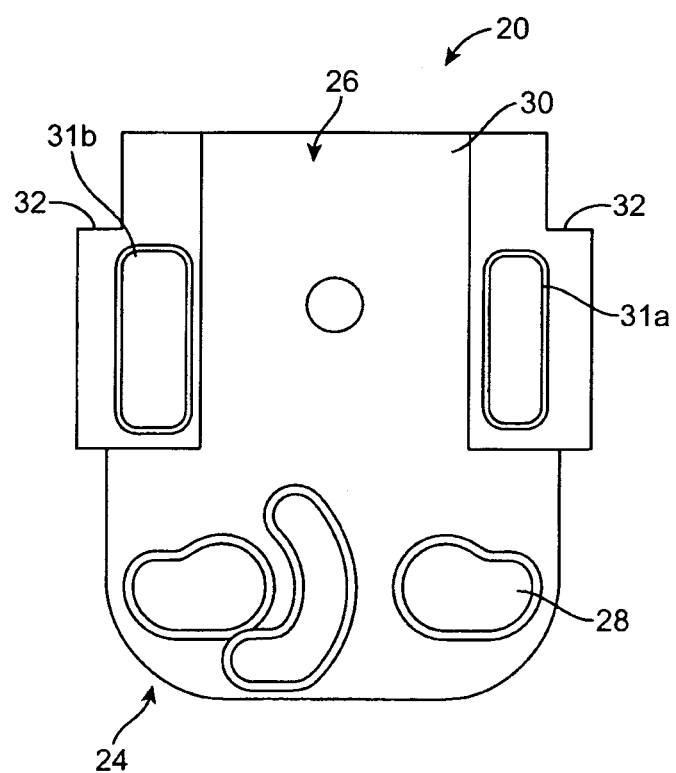
FIG. 2b illustrates a side view of a half of a body of a spacer according to the present invention.
Figure 2C:
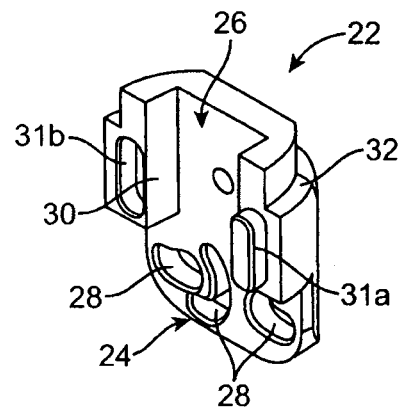
FIG. 2c illustrates a perspective view of another half of a body of a spacer according to the present invention.
Figure 2D:
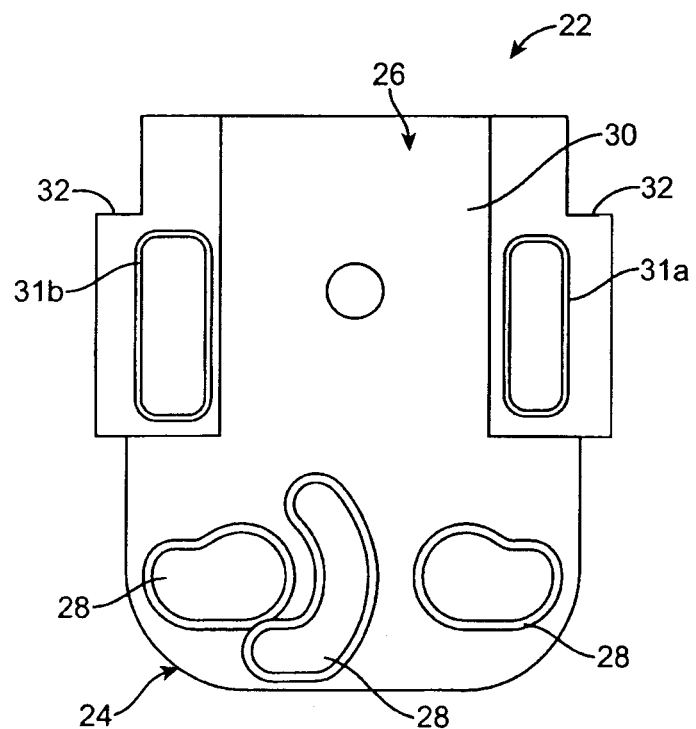
FIG. 2d illustrates a side view of the other half of a body of a spacer according to the present invention.

The outside of the body 12 defines a ledge 32 along at least a portion of the periphery. Notches 34 are formed with the ledge 32 at opposite locations as shown in FIG. 1c. The notches 34 are configured for pronged attachment to a spacer delivery instrument and, as seen in FIG. 1c, are of different width to assist the clinician in orienting the spacer 10 with respect to the spacer delivery instrument. When joined together, the left and right body pieces 20, 22 define a proximal opening 36 (as seen in FIG. 1e) and a distal opening 38 (as seen in FIG. 1a) in the body 12. A longitudinal scallop (of a type shown in FIG. 10 with reference number 78) extending from the proximal end of the spacer to the distal end on either one or both sides of the body and oppositely located, is formed to facilitate placement of the spacer 10 between and to conform to the anatomy of adjacent interspinous processes.

Figure 3A:
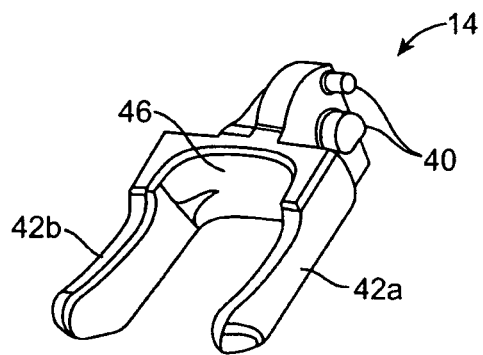
FIG. 3a illustrates a perspective view of a superior arm of a spacer according to the present invention.
Figure 3B:
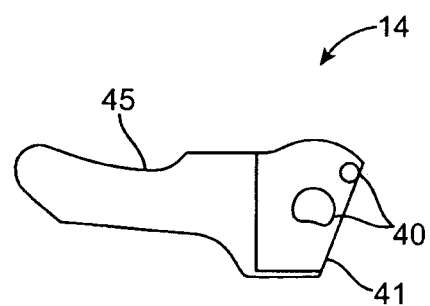
FIG. 3b illustrates a side view of a superior arm of a spacer according to the present invention.
Figure 3C:
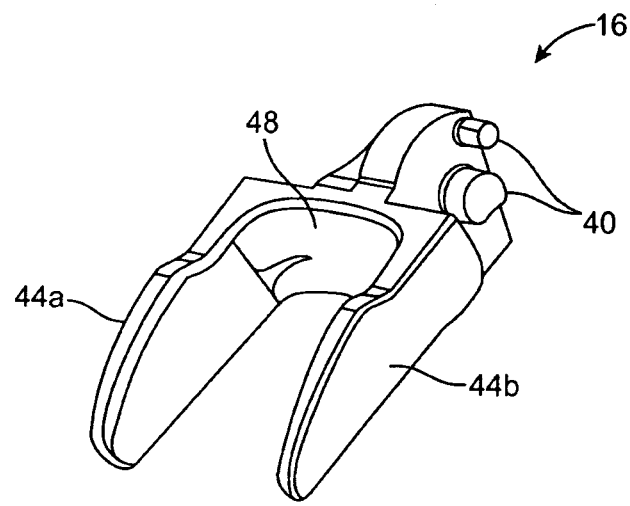
FIG. 3c illustrates a perspective view of an inferior arm of a spacer according to the present invention.
Figure 3D:
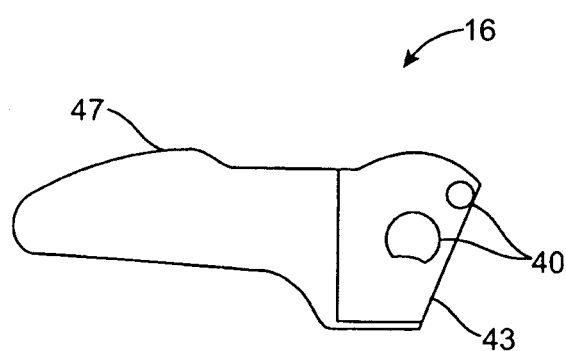
FIG. 3d illustrates a side view of an inferior arm of a spacer according to the present invention.

Turning now to FIGS. 3a and 3b, the superior arm 14 is shown and in FIGS. 3c and 3d, the inferior arm 16 is shown. The superior and inferior arms 14, 16 include pins 40 for mating with the body 12, in particular, for mating with the slots 28 of the arm receiving portion 24. Each of the superior and inferior arms 14, 16 includes at least one camming surface 41, 43, respectively, for contact with the actuator assembly 18. The superior and inferior arms 14, 16 include elongated superior extensions 42a, 42b and elongated inferior extensions 44a, 44b, respectively. Extensions 42a and 44a are located on the left adjacent to the left body piece 20 and extensions 42b and 44b are located on right adjacent to the right body piece 22. Superior extensions 42a, 42b extend substantially parallel to each other in both an undeployed configuration and in a fully-deployed configuration as do inferior extensions 44a, 44b. Extending between extensions 42a, 42b is a strut, bridge, bracket or saddle 46 that forms a superior substantially U-shaped configuration together with the extensions 42a, 42b that is sized and configured to receive a superior spinous process. As seen in FIG. 3b, the anterior face of the superior extensions 14 includes a slight concavity or curvature 45 for conforming to the bony anatomy of the superior spinous process and or lamina. Also, as seen in FIG. 3d, the anterior face of the inferior extensions 16 includes a slight convexity or curvature 47 for conforming to the bony anatomy of the inferior spinous process and or lamina. Also, extending between inferior extensions 44a, 44b is a strut, bridge, bracket or saddle 48 that forms an inferior substantially U-shaped configuration together with the extensions 44a, 44b that is sized and configured to receive an inferior spinous process of a spinal motion segment.

Figure 4:
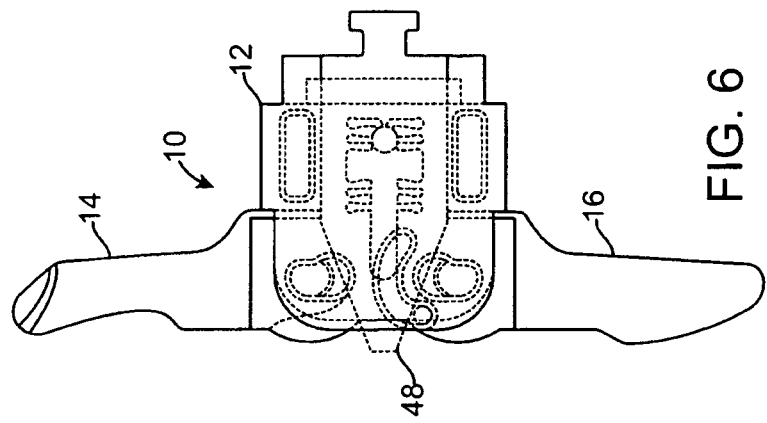
FIG. 4 illustrates a side, semi-transparent view of a spacer in a deployed configuration according to the present invention.
Figure 5:
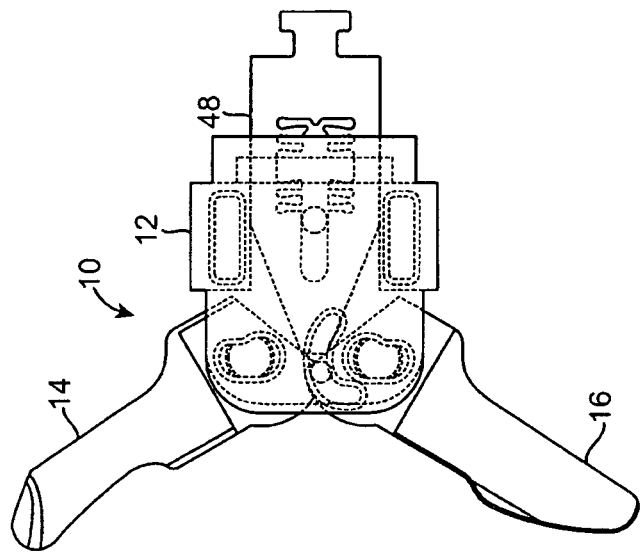
FIG. 5 illustrates a side, semi-transparent view of a spacer in a partially deployed configuration according to the present invention.
Figure 6:
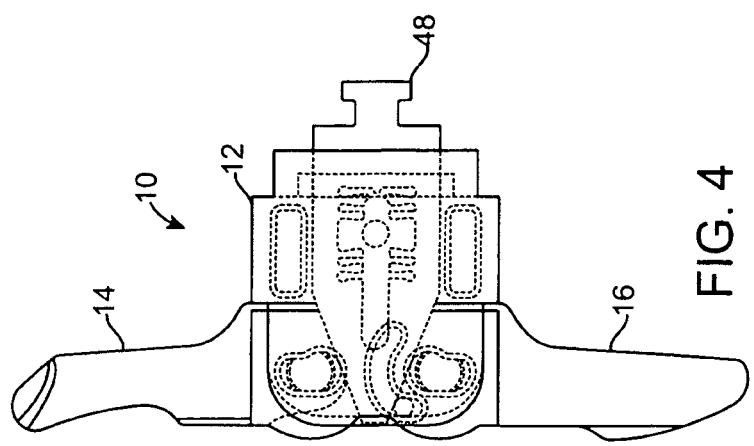
FIG. 6 illustrates a side, semi-transparent view of a spacer in a deployed and extended configuration according to the present invention.

The superior and inferior arms 14, 16 are movably or rotatably connected to the body 12, for example by hinge means or the like to provide rotational movement from an undeployed configuration to a deployed configuration that arcs through approximately a 90 degree range or more. The arms 14, 16 are rotationally movable between at least an undeployed, collapsed or folded state (as shown in FIGS. 1a-1e) and at least a fully deployed state (as shown in FIG. 4). One of many partially deployed states through which the arms move between the fully undeployed and fully deployed state is shown in FIG. 5. In the undeployed state, the arm pairs 14, 16 are aligned generally or substantially axially (i.e., axially with the longitudinal axis defined by the body 12 or to the translation path into the interspinous space of the patient) to provide a minimal lateral or radial profile. The longitudinal axis X of the body is shown in FIG. 1c. In the deployed state, the arm pairs 14, 16 are positioned such that the U-shaped saddles are in a plane or have a U-shaped projection in a plane that is generally or substantially transverse to the longitudinal axis X defined by the body 12 or to the collapsed position or to the translation path into the interspinous space of the patient. The arms 14, 16 may also be linearly moveable or translatable within the plane from a first deployed state to and from a second deployed state characterized by an additional extension of at least one of the arms 14, 16 along the direction of the arrows as shown in FIG. 6. More specifically, the arms 14, 16 can be extended in the general vertical direction along an axis substantially parallel to the spine wherein the arms 14, 16 are extended away from each other and away from the body 12 as denoted by the arrows in FIG. 6. This feature advantageously allows for the most minimally invasive configuration for the spacer without compromising the ability to seat and contain the spinous processes in between levels where the process anatomy in such that the interspinous process space increases in the anterior direction or without compromising the ability of the spacer to provide adequate distraction. The arms 14, 16 are connected to the body 12 and/or to each other in a manner that enables them to be moved simultaneously or independently of each other, as well as in a manner that provides passive deployment and/or vertical extension or, alternatively, active or actuated deployment and/or vertical extension.

Figure 7A:
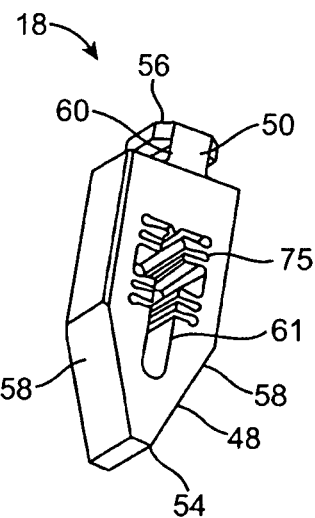
FIG. 7a illustrates a perspective view of an actuator assembly of a spacer according to the present invention.
Figure 7B:
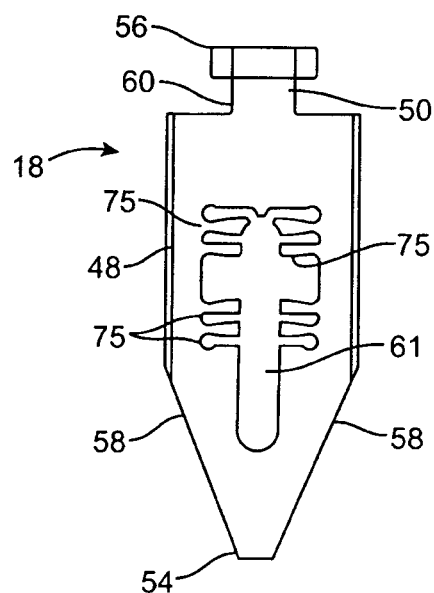
FIG. 7b illustrates a side view of an actuator assembly of a spacer according to the present invention.

Turning now to FIGS. 7a and 7b, the actuator assembly 18 will now be described. The actuator assembly 18 includes an actuator 48 connected to a shaft 50. The actuator 48 includes a distal end 54 and a proximal end 56 and at least two bearing surfaces 58. The bearing surfaces 58 angle towards each other from the proximal end 54 to the distal end 56. The shaft 50 has a substantially reduced cross-sectional area and includes a neck 60 for connection with a spacer insertion instrument. The actuator assembly is at least partially disposed inside the body and is configured for sliding engagement with respect to the body. The actuator 48 includes a slot 61 for receiving an actuator pin 52 seen in FIG. 1d that is connected to the body. The actuator 48, with the pin 52 passed through the slot 61, is connected to the body in sliding engagement. The distal end of the actuator shaft is further configured to engage the superior and inferior arms 14, 16 such that forward translation of the actuator relative to the body effects deployment of the arms into at least one deployed configuration. The at least one deployed configuration can be selectively locked into position via the actuator pin 52 riding inside the slot in the actuator shaft and engaging several fingers 75 forming one or more constrictions along the slot path. The constrictions are configured to lock the pin 52 keeping it fixed in at least one desired deployed configuration in a friction fit engagement. Four sets of fingers 75 grouped in two sets of two oppositely located sets of fingers 75 are shown in FIG. 7b and are configured such that the pin 52 is capable of entering two locked locations between the sets of fingers 75. Typically, a first locked location locks the arms in a deployed configuration and the second locked location locks the arms in an extended-deployed location wherein the pin 52 is resident between two oppositely located sets of fingers when in the at least one locked location. The fingers 75 flex to corral the pin in place.

Figure 8:
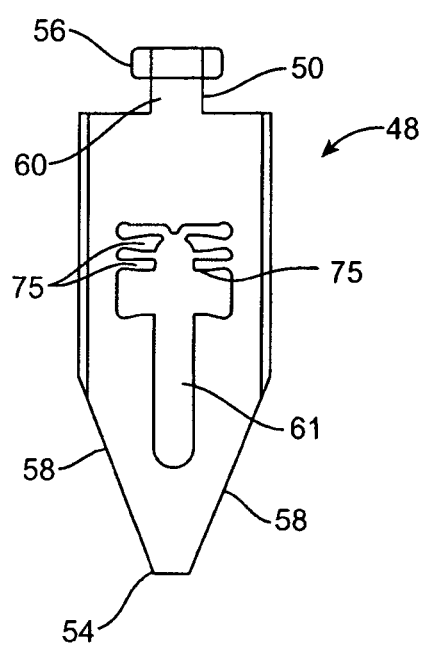
FIG. 8 illustrates a side view of an actuator assembly of a spacer according to the present invention.
Figure 8A:
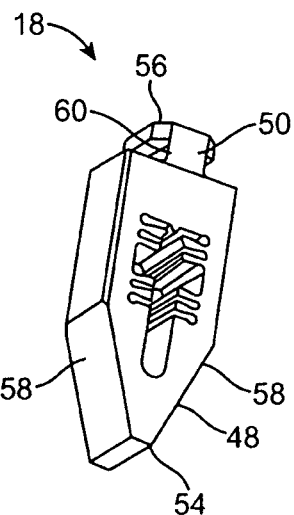
Figure 8B:
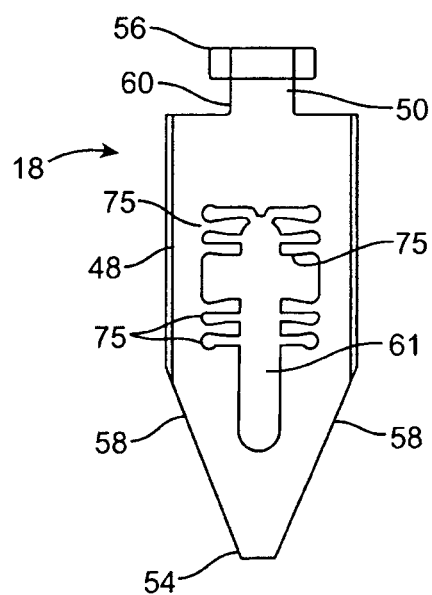

Another variation of the actuator 48 is shown in FIG. 8. The actuator 48 includes an actuator 48 connected to a shaft 50. The actuator assembly includes a distal end 54 and a proximal end 56 and at least two bearing surfaces 58. The bearing surfaces 58 angle towards each other from the proximal end 54 to the distal end 56. The shaft 50 has a substantially reduced cross-sectional area and includes a neck 60 for connection with a spacer insertion instrument. The actuator includes several fingers 75 forming one or more constrictions along the slot 61 path. The constrictions are configured to lock the pin 52 keeping it fixed in at least one desired deployed configuration in a friction fit engagement. One set of fingers 75 are shown in FIG. 8 and are configured such that the pin 52 is pressed in the fingers when in one deployed configuration.

With reference to FIGS. 9a-9e, various views of another variation of a spacer 10 according to the present invention are shown wherein like reference numbers are used to describe like parts. The spacer 10 includes a body 12, a superior extension member or arm 14, an inferior extension member or arm 16, and an actuator assembly 18.

Figure 10:
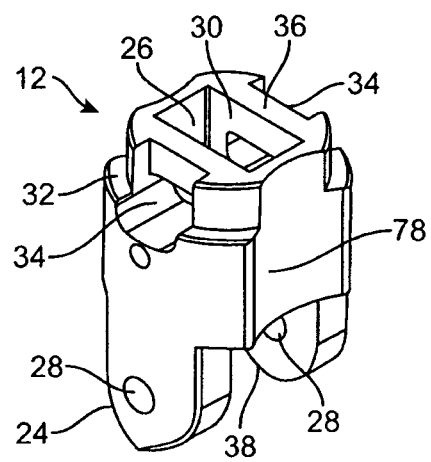
FIG. 10 illustrates a perspective view of a body of a spacer according to the present invention.

Turning now to FIG. 10, the body 12 will now be described. The body 12 is shown to have a one-piece construction; however, the body 12 may be configured into a clamshell with two mating pieces joined together as described above. The body 12 has a cross-sectional size and shape that allows for implantation between adjacent spinous processes and facilitates delivery into a patient through a narrow port or cannula.

The inside of the body 12 defines an arm receiving portion 24 and an actuator assembly receiving portion 26 with features formed therein that together define the arm and actuator assembly receiving portions 24, 26. In one variation, the arm receiving portion 24 includes slots 28 that receive one or more pins to capture the arms 14, 16 such that the arms can hinge about the pin. As shown in FIG. 10, the slots 28 are formed in flange-like extensions of the body. The actuator assembly receiving portion 26 includes a passageway 30 that conforms to the shape of the actuator.

Figure 9A:
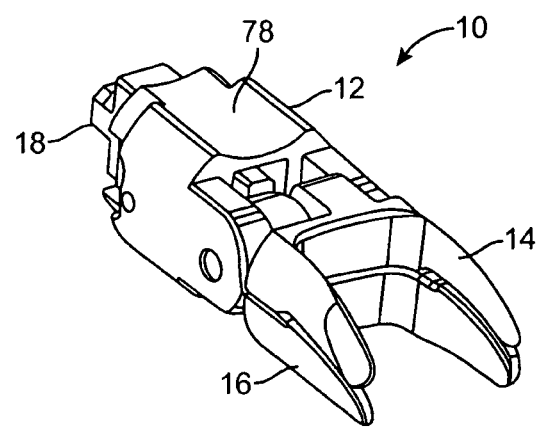
FIG. 9a illustrates a perspective view of a spacer according to the present invention.
Figure 9B:
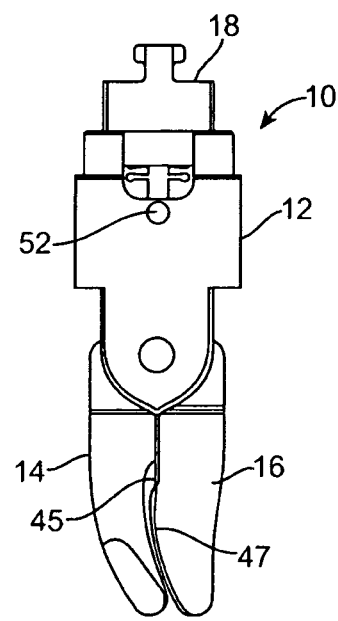
FIG. 9b illustrates a side view of a spacer according to the present invention.
Figure 9C:
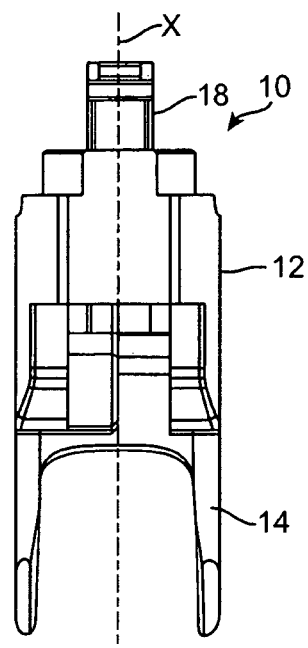
FIG. 9c illustrates a top view of a spacer according to the present invention.
Figure 9D:
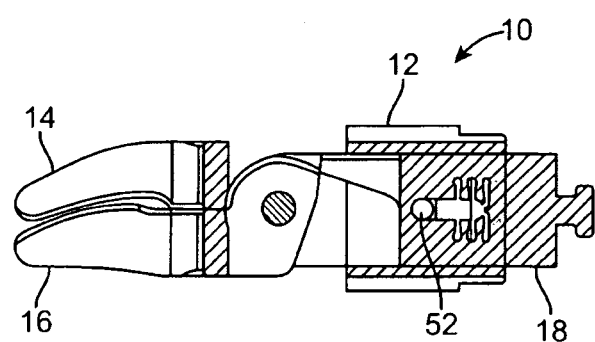
FIG. 9d illustrates a cross-sectional view of the spacer of FIG. 9c taken along line X according to the present invention.
Figure 9E:
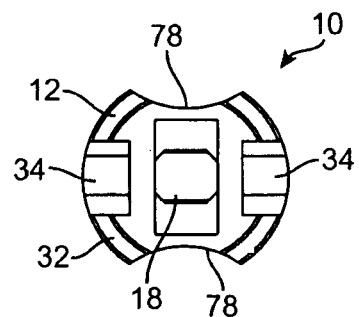
FIG. 9e illustrates an end view of a spacer according to the present invention.

Still referencing FIG. 10, the outside of the body 12 defines a ledge 32 along at least a portion of the periphery. Notches 34 (also shown in FIG. 9e) are formed with the ledge 32 at opposite locations. The notches 34 are configured for pronged attachment to a spacer delivery instrument such that a portion of the spacer delivery instrument securely connects with the body. The body 12 defines a proximal opening 36 and a distal opening 38. A longitudinal scallop 78 extending from the proximal end of the spacer to the distal end on either one or both sides and oppositely located, is formed to facilitate placement of the spacer 10 between and to conform to the anatomy of adjacent interspinous processes. The longitudinal scallops 78 are also shown in FIGS. 9a and 9e.

Figure 11A:
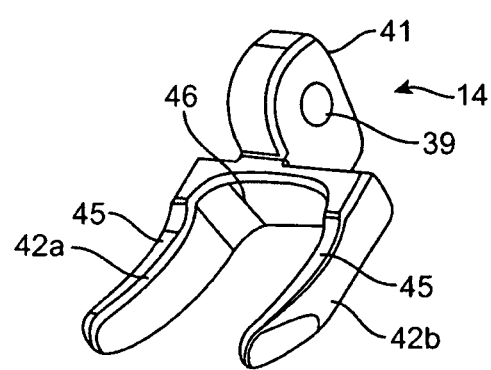
FIG. 11a illustrates a perspective view of a superior arm of a spacer according to the present invention.
Figure 11B:
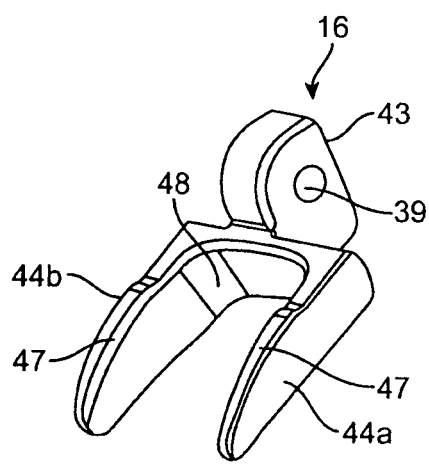
FIG. 11b illustrates a perspective view of an inferior arm of a spacer according to the present invention.

Turning now to FIGS. 11a and 11b, there are shown figures of the superior arm 14 and the inferior arm 16, respectively. The superior and inferior arms 14, 16 include apertures 39 for receiving a pin for pinned connection and rotation with respect to the body 12. Each of the superior and inferior arms 14, 16 includes at least one camming surface 41, 43, respectively, for contact with the actuator assembly 18. The superior and inferior arms 14, 16 include elongated superior extensions 42a, 42b and elongated inferior extensions 44a, 44b, respectively. Extensions 42a and 44a are located on one side of the body and extensions 42b and 44b are located on the other side of the body. Superior extensions 42a, 42b extend substantially parallel to each other in both an undeployed configuration and in a deployed configuration as do inferior extensions 44a, 44b. Extending between extensions 42a, 42b is a strut, bridge, bracket or saddle 46 that forms a superior substantially U-shaped configuration together with the extensions 42a, 42b that is sized and configured to receive and seat or contain at least a portion a superior spinous process. As seen in FIGS. 9b and 11a, the anterior deployed face of the superior extensions 14 includes a slight concavity 45 for conforming to the bony anatomy of the superior spinous process and or lamina. Also, as seen in FIGS. 9b and 11b, the anterior deployed face of the inferior extensions 16 includes a slight convexity 47 for conforming to the bony anatomy of the inferior spinous process and or lamina. Extending between inferior extensions 44a, 44b is a strut, bridge, bracket or saddle 48 that forms an inferior substantially U-shaped configuration together with the extensions 44a, 44b that is sized and configured to receive and seat at least a portion of an inferior spinous process of a spinal motion segment.

The superior and inferior arms 14, 16 are movably or rotatably connected to the body 12, for example by a pin or hinge means or the like to provide rotational movement to and from an undeployed configuration to a deployed configuration that arcs through approximately a 90 degree range or more. The arms 14, 16 are rotationally movable between at least an undeployed, collapsed or folded state (as shown in FIGS. 9a-9e) and at least a fully deployed state (as shown in FIGS. 4 and 6). A partially deployed state through which the arms move between the undeployed and deployed state is shown in FIG. 5. In the undeployed state, the arm pairs 14, 16 are aligned generally or substantially axially (i.e., axially with the longitudinal axis defined by the body 12 or to the translation path into the interspinous space of the patient) to provide a minimal lateral or radial profile. The longitudinal axis X of the body is shown in FIG. 9c. In the deployed state, the arm pairs 14, 16 are positioned in a plane generally or substantially transverse to the collapsed position (i.e., in a plane transverse to the longitudinal axis X defined by the body 12 or to the translation path into the interspinous space of the patient). The arms 14, 16 are connected to the body 12 and/or to each other in a manner that enables them to be moved simultaneously or independently of each other, as well as in a manner that provides passive deployment and/or vertical extension or, alternatively, active or actuated deployment and/or vertical extension.

Figure 12A:
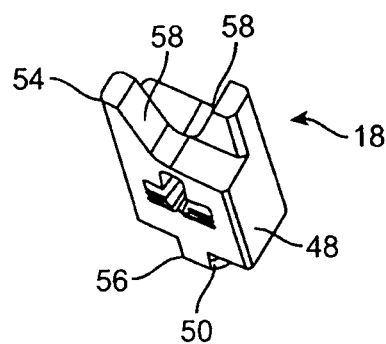
FIG. 12a illustrates a perspective view of an actuator assembly of a spacer according to the present invention.
Figure 12B:
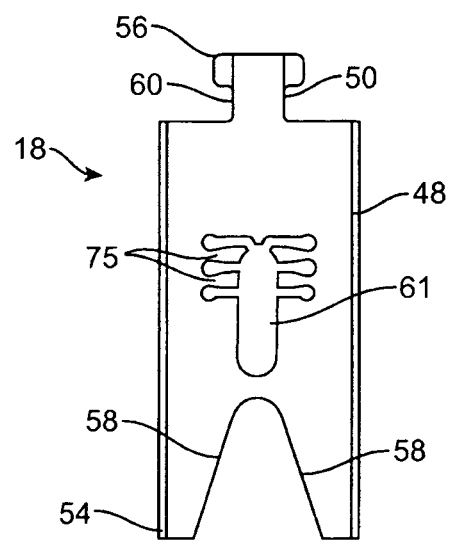
FIG. 12b illustrates a side view of an actuator assembly of a spacer according to the present invention.

Turning now to FIGS. 12a and 12b, the actuator assembly 18 will now be described. The actuator assembly 18 includes an actuator 48 connected to a shaft 50. The actuator 48 includes a distal end 54 and a proximal end 56 and at least two bearing surfaces 58. The bearing surfaces 58 angle away from each other from the proximal end 54 to the distal end 56. Furthermore, the bearing surfaces are displaced laterally from each other. The shaft 50 has a substantially reduced cross-sectional area forming a neck or receiving portion 60 for connection with a spacer insertion instrument. The actuator assembly 18 is at least partially disposed inside the body and is configured for sliding engagement with respect to the body. The actuator 48 includes a slot 61 for receiving an actuator pin 52 seen in FIGS. 9b and 9d that is connected to the body. The actuator 48, with the pin 52 passed through the slot 61, is connected to the body in sliding engagement. The distal end 54 of the actuator 48 is further configured to engage the superior and inferior arms 14, 16 such that forward translation of the actuator relative to the body 12 effects deployment of the arms 14, 16 into at least one deployed configuration. The at least one deployed configuration can be selectively locked into position via the actuator pin 52 riding inside the slot in the actuator shaft and engaging several fingers 75 forming one or more constrictions along the slot path. The constrictions are configured to lock the pin 52 keeping it and the deployed arms fixed in at least one desired deployed configuration in a friction fit engagement. One set of fingers 75 is shown in FIG. 12b which is configured such that the pin 52 is resident between the fingers when in one deployed configuration.

General assembly of the spacers 10 discussed above will now be described. The arms 14, 16 are disposed in the arm receiving portion 24 of one body piece. The other of the left or right body piece 20, 22 is securely connected/welded to the one body piece thereby capturing the arms 14, 16 inside the arm receiving portion 24 such that the arms 14, 16 are capable of at least rotational movement with respect to the body 12 and in one variation, capable of rotational movement and translation with respect to the body 12. In the variation in which the body 12 is made of one piece, the arms 14, 16 are movably connected to the body 12 with a pin. The actuator assembly 18 is inserted into the passageway 30 of the body 12 and a pin 52 is passed through the body 12 and into the slot 61 of the actuator 48 securing the actuator assembly 18 to the body 12 such that the actuator 48 is allowed to slide with respect to the body 12.

To deliver and deploy the spacer 10 within the patient, the spacer 10 is releasably attached to a delivery instrument at the proximal end of the spacer 10 via notches 34. The delivery instrument will now be described in greater detail.

Figure 13C:
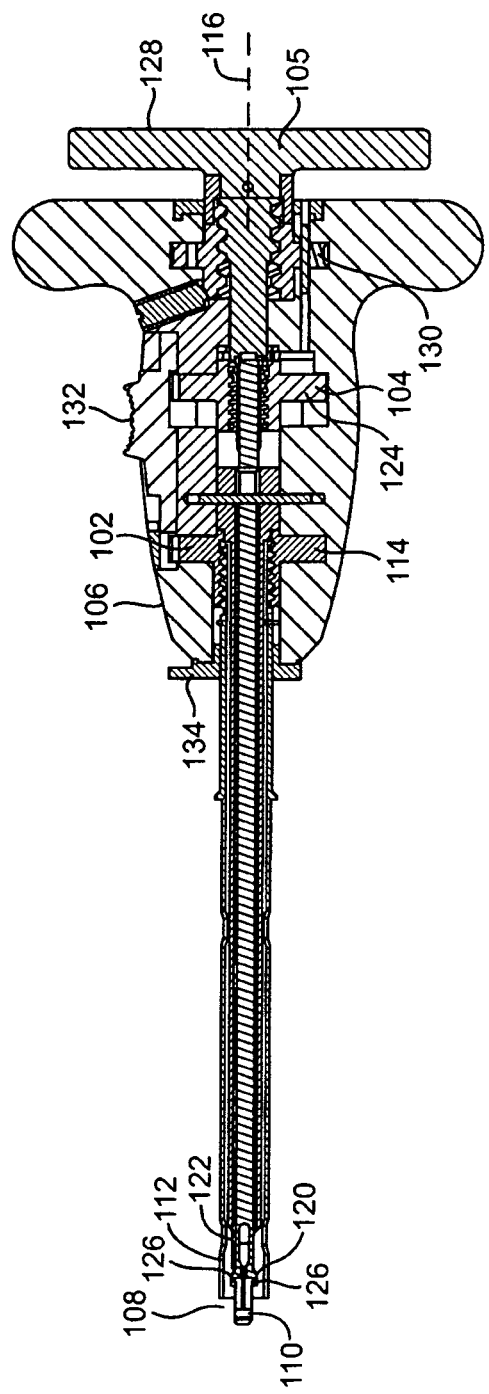
FIG. 13c illustrates a cross-sectional view of a spacer insertion instrument according to the present invention.

Turning now to FIGS. 13a-13c, there is shown an insertion instrument 100 according to the present invention. The insertion instrument 100 includes a first subassembly 102, a second subassembly 104 and a third subassembly 105 connected to a handle assembly 106.

Figure 13D:
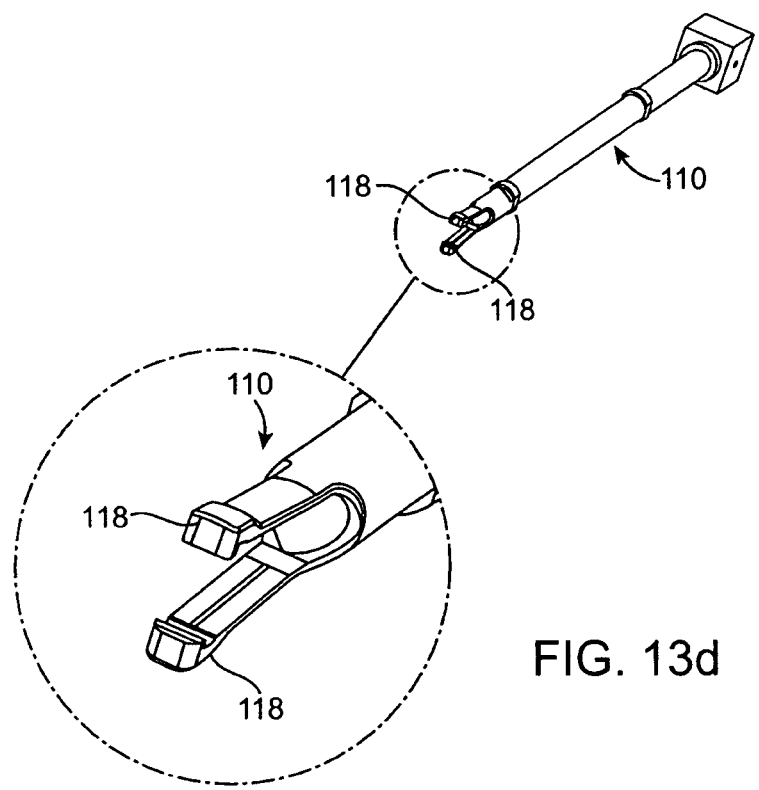
FIG. 13d illustrates a perspective view of a clamp shaft of a spacer insertion instrument according to the present invention.
Figure 14D:
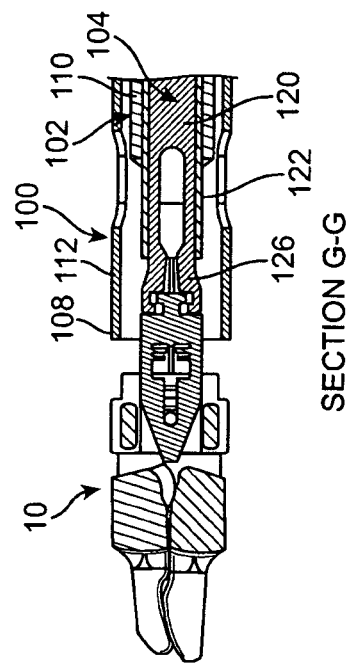
FIG. 14d illustrates a cross-sectional view taken along line G-G of FIG. 14b of a spacer insertion instrument in juxtaposition to a spacer according to the present invention.
Figure 14C:
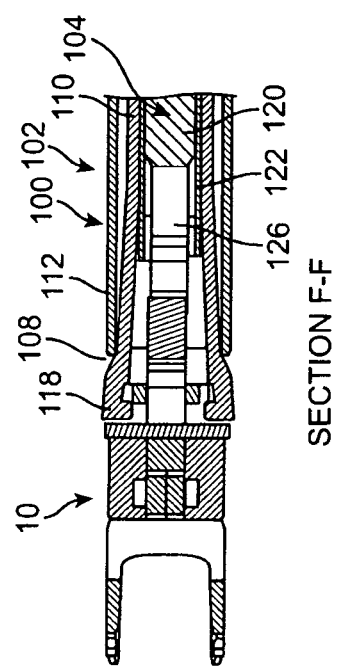
FIG. 14c illustrates a cross-sectional view taken along line F-F of FIG. 14a of a spacer insertion instrument in juxtaposition to a spacer according to the present invention.

The first subassembly 102 is configured to releasably clamp to the body 12 of the spacer 10 at a distal end 108 of the insertion instrument. Still referencing FIGS. 13a-13c, the first subassembly 102 includes a first clamp shaft 110 and a first outer shaft 112 configured for relative motion with respect to one another via a first control 114 located at the handle assembly 106. With particular reference to FIG. 13c, the first control 114 is threaded to the first outer shaft 112 such that rotation of the first control 114 moves the first outer shaft 112 along the longitudinal axis 116 of the insertion instrument 100. Reverse rotation of the first control 114 reverses the direction of translation of the first outer shaft 112. The first clamp shaft 110 is shown in FIG. 13d. The first clamp shaft 110 is a cannulated shaft fixed to the handle assembly 106 and configured to be received inside the cannulated first outer shaft 112. The first clamp shaft 110 includes two oppositely located, outwardly splayed prongs 118 that are permitted to flex inwardly and return to their outwardly splayed normal position as shown in FIG. 13d when released. The prongs 118 are configured to be clamped into the notches 34 formed in the spacer body 12 to clamp onto and securely hold the spacer 10 to the insertion instrument 100. As the first outer shaft 112 is translated distally in sliding motion with respect to the first clamp shaft 110 by rotating the first control 114 in one direction, the first outer shaft 112 is configured to advance over the outwardly splayed prongs 118 and deflect them inwardly to clamp into a properly oriented, juxataposed spacer body 12. When the first outer shaft 112 is translated proximally with respect to the first clamp shaft 110 by rotating the first control in an opposite direction, the first outer shaft 112 is configured to uncover the prongs 118 allowing them to flex outwardly to their normal outwardly splayed configuration to release a spacer 10 to which it is connected.

The second subassembly 104 is configured to releasably clamp to the actuator 48 of the spacer 10 at the distal end 108 of the insertion instrument 100. The second subassembly 104 includes a second clamp shaft 120 and a second outer shaft 122 configured for relative motion with respect to one another via a second control 124 located at the handle assembly 106. The second control 124 is threaded to the second outer shaft 122 such that rotation of the second control 124 moves the second outer shaft 122 along the longitudinal axis 116 of the insertion instrument 100. Reverse rotation of the second control 124 reverses the direction of translation of the second outer shaft 122. The second clamp shaft 120 is shown in FIG. 13c and is similar to the first clamp shaft 110 except that it is positioned approximately 90 degrees with respect to the first clamp shaft 110. The second clamp shaft 120 is a connected to the third subassembly 105 and configured to be received inside the cannulated second outer shaft 122. Both the second clamp shaft 120 and the second outer shaft 122 are located concentrically inside the first clamp shaft 110. The second subassembly 104 is located concentrically inside the first subassembly 102. The second clamp shaft 120 includes two oppositely located, outwardly splayed prongs 126 that are permitted to flex inwardly and return to their outwardly splayed normal position. The prongs 126 are configured to be clamped to the actuator 48 of the spacer 10, and in particular, to the proximal end 56 of the actuator 48 at the neck receiving portion 60 of the actuator shaft 50. Any suitable interface may be formed for connecting to the actuator 48. As the second outer shaft 122 is translated distally with respect to the second clamp shaft 120 by rotating the second control 124 in one direction, the second outer shaft 112 is configured to advance over the outwardly splayed prongs 126 and deflect them inwardly to connect to the actuator 48 of a juxataposed spacer 10. When the second outer shaft 122 is translated proximally with respect to the second clamp shaft 120 by rotating the second control 124 in an opposite direction, the second outer shaft 122 is configured to uncover the prongs 126 allowing them to flex outwardly to their normal outwardly splayed configuration to release the actuator 48 of the spacer 10 to which it is connected.

The third subassembly 105 is configured to translate the entire second subassembly 104 with respect to the handle assembly 106 (or, in another variation, with respect to the first subassembly 102) to thereby translate the actuator 48 of a spacer 10 with respect to the body 12 of the spacer to arrange the spacer to and from deployed and undeployed configurations. The third subassembly 105 includes a proximally located third control 128 configured in the form of a removable drive handle threaded to the second assembly 104 and configured for effecting relative motion of the second assembly 104 with respect to the handle assembly 106 wherein rotation of the drive handle 128 moves the second assembly 104 along the longitudinal axis 116 of the insertion instrument 100. Reverse rotation of the drive handle 128 reverses the direction of translation of the second assembly 104. Because the second assembly 104 is connected to the actuator 48 of the spacer 10 such longitudinal translation effects translation of the actuator 48 with respect to the body 12 of the spacer 10. In one variation, the third assembly 105 further includes a fourth control 130 for adjusting the position of the second assembly 104 relative to the handle assembly 106 such that differently-sized spacers are easily connectable to the insertion instrument at the distal end. For example, as shown in FIG. 13b, a setting of large L on the fourth control 130 positions the second assembly 104 proximally with respect to the handle assembly 106 such that a spacer with a longitudinally longer body 12 may be easily accepted and connected to the insertion instrument 100 at the distal end 108. A setting of small S on the fourth control 130 positions the second assembly 104 distally with respect to the handle assembly 106 such that a spacer with a longitudinally shorter body 12 may be easily accepted and connected to the insertion instrument 100 at the distal end 108. The fourth control 130 may also be employed simultaneously or independently of the third control 128 to arrange the spacer to and from deployed and undeployed configurations.

Other features of the insertion instrument 100 include a lock 132 configured to lock the first and second subassemblies 102, 104 into position to prevent accidental release of the spacer body 12 or spacer actuator 12. A direction indicator 134 is provided on the instrument 100 for orientating the instrument 100 with respect to the patient anatomy. In one variation, for example, the direction indicator 134 indicates a cephalad orientation. Various depth markings 136 are also provided as well as connection arrows for lining up the spacer with respect to the instrument.

Turning now to FIGS. 14a-14d, the operation of the spacer 10 and insertion instrument 100 will now be discussed. In operation, the fourth control 130 is adjusted for the size of spacer 10 to be connected to the insertion instrument 100. If a longitudinally large spacer 10 is to be connected, the fourth control 130 is set to large. If a longitudinally small spacer 10 is to be connected, the fourth control 130 is set to small. This selection positions the distal end of the second assembly 104 proximally or distally with respect to the distal end 108 of the instrument 10 for attachment to the actuator 48. The spacer 10 is then positioned proximate to the distal end 108 of the insertion instrument 100. The spacer 10 is provided or otherwise placed in its undeployed state next to the distal end 108 of the instrument. Initially, the prongs 118, 126 are not engaged as shown in FIGS. 14a-14d.

Figure 15C:
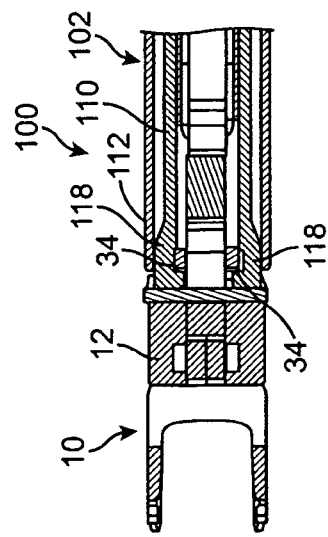
FIG. 15c illustrates a cross-sectional view taken along line G-G of FIG. 15a of a spacer insertion instrument connected to a spacer according to the present invention.
Figure 15D:
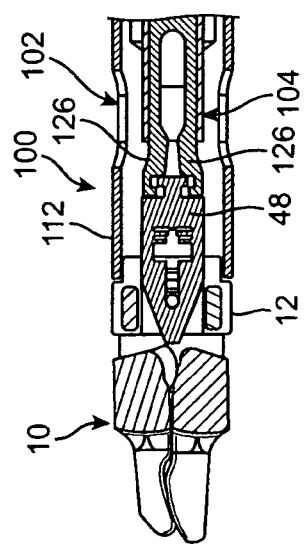
FIG. 15d illustrates a cross-sectional view taken along line F-F of a FIG. 15b of a spacer insertion instrument connected to a spacer according to the present invention.
Figure 16D:
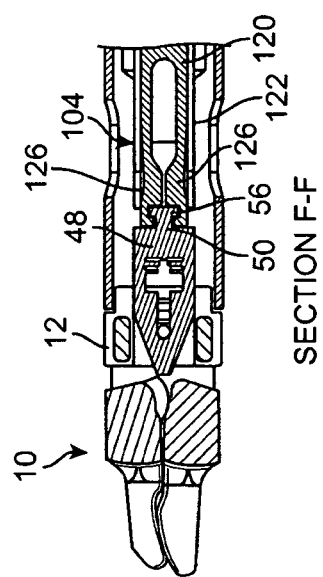
FIG. 16d illustrates a cross-sectional view taken along line F-F of FIG. 16b of a spacer insertion instrument connected to a spacer according to the present invention.
Figure 16C:
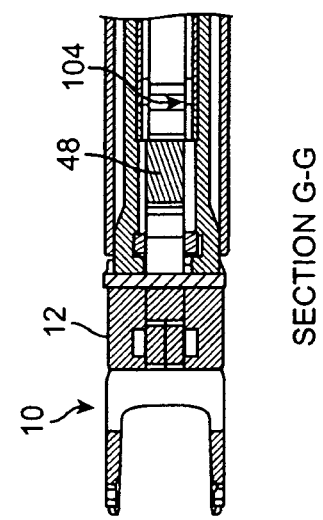
FIG. 16c illustrates a cross-sectional view taken along line G-G of FIG. 16a of a spacer insertion instrument connected to a spacer according to the present invention.
Figure 17D:
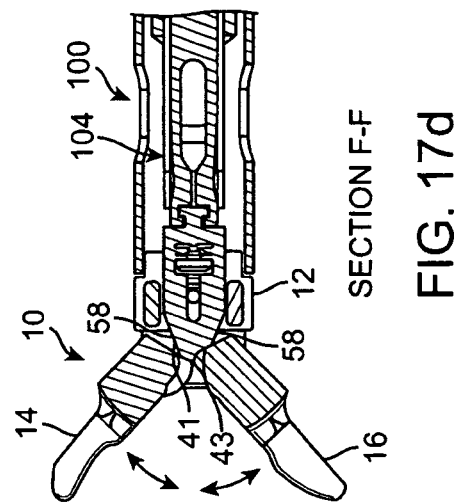
FIG. 17d illustrates a cross-sectional view taken along line F-F of FIG. 17b of a spacer insertion instrument connected to a spacer according to the present invention.
Figure 17C:
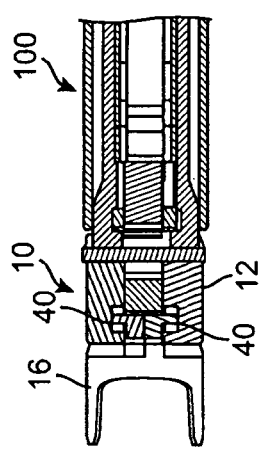
FIG. 17c illustrates a cross-sectional view taken along line G-G of FIG. 17a of a spacer insertion instrument connected to a spacer according to the present invention.
Figure 18D:
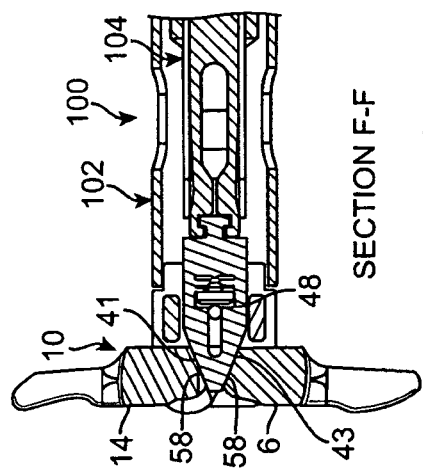
FIG. 18d illustrates a cross-sectional view taken along line F-F of FIG. 18b of a spacer insertion instrument connected to a spacer in a deployed configuration according to the present invention.
Figure 18C:
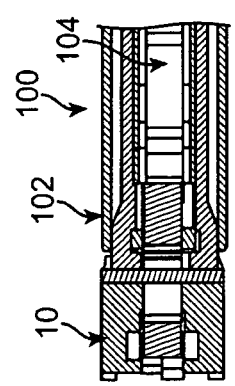
FIG. 18c illustrates a cross-sectional view taken along line G-G of FIG. 18a of a spacer insertion instrument connected to a spacer in a deployed configuration according to the present invention.

Turning now to FIGS. 15a-15d, the first control 114 is activated at the handle of the insertion instrument 100 such that the first subassembly 102 is connected to the body 12 of the spacer 10. The first control 114 is rotated in one direction to advance the first outer shaft 112 over the first clamp shaft 110 deflecting the prongs 118 inwardly into the notches 34 on the body of the spacer 12 to secure the spacer body 12 to the instrument as shown clearly in FIG. 15c. FIG. 15d shows that the prongs 126 of the second subassembly 104 are not connected to the actuator 48.

Turning now to FIGS. 16a-16d, the second control 124 is activated at the handle of the insertion instrument such that the second subassembly is connected to the actuator 48 of the spacer 10. The second control 124 is rotated in one direction to advance the second outer shaft 122 over the second clamp shaft 120 deflecting the prongs 126 inwardly to clamp onto the proximal end 56 of the actuator shaft 50 to secure the actuator 48 to the instrument 100 as shown clearly in FIG. 16d. Although described such that the first subassembly 102 is first connected to the body 12, the instrument 100 may be employed such that the second subassembly 104 is connected first to the actuator and then the first subassembly 102 is connected to the body. With both the first and second subassemblies 102, 104 connected to the spacer 10, the lock 132 is pushed to lock the first and second subassemblies 102, 104 in place to prevent accidental detachment.

To deliver and deploy the spacer 10 within the patient, the spacer 10 is releasably attached to a delivery instrument 100 at the proximal end of the spacer 10 as described. A small midline or lateral-to-midline incision is made in the patient for minimally-invasive percutaneous delivery. In one variation, the supraspinous ligament is split longitudinally along the direction of the tissue fibers to create an opening for the instrument. Dilators may be further employed to create the opening. In the undeployed state with the arms 14, 16 in a closed orientation and attached to a delivery instrument, the spacer 10 is inserted into a port or cannula, if one is employed, which has been operatively positioned in an interspinous space within a patient's back and the spacer is passed through the cannula to the interspinous space between two adjacent vertebral bodies. The spacer 10 is advanced beyond the end of the cannula or, alternatively, the cannula is pulled proximally to uncover the spacer 10 connected to the instrument 100. Once in position, the third control 128 and/or fourth control 130 is rotated to begin the deployment of at least one of the superior arm 14 and inferior arm 16 or both simultaneously. FIGS. 17a-17d illustrate the superior arm 14 and the inferior arm 16 in a partially deployed position with the arms 14, 16 rotated away from the longitudinal axis 116 and the second subassembly 104 advanced distally with respect to the body of the spacer 12. Distal advancement of the second subassembly 104 which is connected to the actuator 48, in turn, distally advances the actuator 48 whose bearing surfaces 58 contact the superior and inferior camming surfaces 41, 43 pushing the superior and inferior arms 14, 16 into rotation about the pins 40. The position of the arms 14, 16 in FIGS. 17a-17d may be considered to be one of many partially deployed configurations that are possible and from which the deployment of the arms 14, 16 is reversible with opposite rotation of the third and/or fourth controls 128, 130.

Turning to FIGS. 18a-18d, there is shown an insertion instrument 100 connected to a spacer 10 in a first deployed configuration in which the arms 14, 16 are approximately 90 degrees perpendicular to longitudinal axis 116 or perpendicular the initial undeployed configuration. Continued rotation of third and fourth controls 128, 130 moves the second subassembly 104 further distally with respect to the body 12 of the spacer 10 pushing the bearing surfaces 58 further against the superior and inferior camming surfaces 41, 43. While in the first deployed configuration, the clinician can observe with fluoroscopy the positioning of the spacer 10 inside the patient and then choose to reposition the spacer if desired. Repositioning of the spacer may involve undeploying the arms 14, 16 rotating them into any one of the many undeployed configurations. The spacer may then be re-deployed into the desired location. This process can be repeated as necessary until the clinician has achieved the desired positioning of the spacer in the patient.

Figure 19:
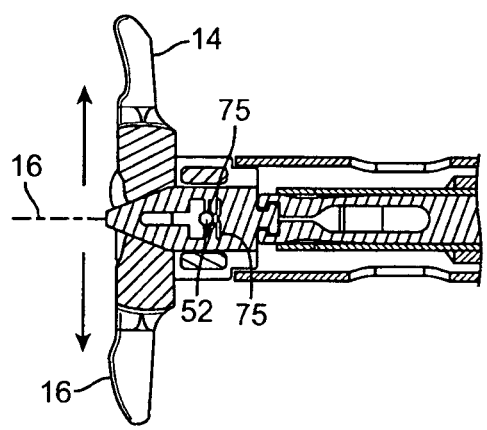
FIG. 19 illustrates a partial cross-sectional view of a spacer insertion instrument connected to a spacer in a deployed and extended configuration according to the present invention.

Even further advancement of the second subassembly 104 from the first deployed configuration results in the spacer assuming a second deployed configuration shown in FIG. 19. The second deployed configuration is an extended configuration in which the superior and inferior arms 14, 16 extend transversely with respect to the longitudinal axis 116 outwardly in the direction of the arrows in FIG. 19. Such extension is guided by the length and shape of the slots 28 in which the arms 14, 16 move. Once deployed, the superior arm 14 seats the superior spinous process and the inferior arm 16 seats the adjacent inferior spinous process. Such extension may also provide some distraction of the vertebral bodies. As seen in this deployed configuration shown in FIG. 19, the actuator pin 52 is seated between the fingers 75 and locked therein.

Figure 20:
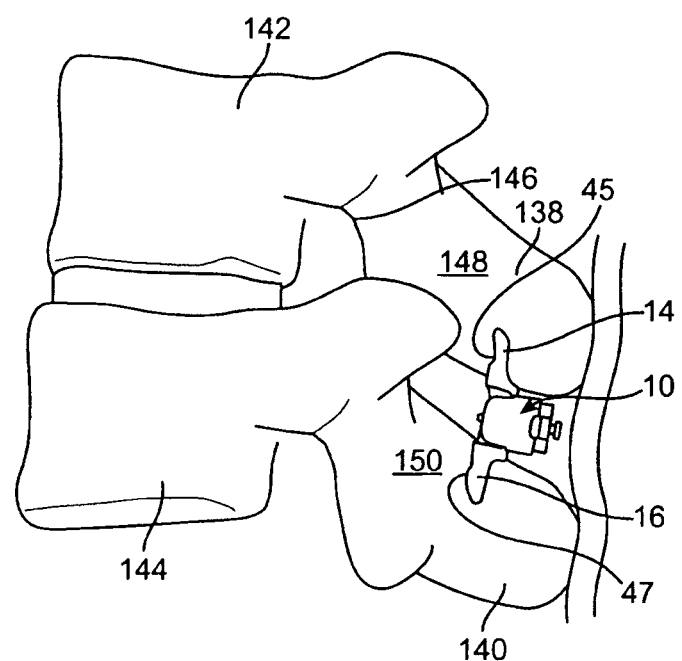
FIG. 20 illustrates a spacer according to the present invention deployed in an interspinous process space between two vertebral bodies and a supraspinous ligament.

Following deployment, the lock 132 is released to permit rotation of the first and second controls 114, 124 which are rotated in the opposite direction to release the body 12 and the actuator 48 from the instrument 100, respectively. The insertion instrument 100, thus released from the spacer, is removed from the patient leaving the spacer 10 implanted in the interspinous process space as shown in FIG. 20. In FIG. 20, the spacer 10 is shown with the superior arm 14 seating the superior spinous process 138 of a first vertebral body 142 and the inferior arm 16 seating the inferior spinous process 140 of an adjacent second vertebral body 144 providing sufficient distraction to open the neural foramen 146 to relieve pain. As mentioned above, the shape of the superior arm 14 is such that a superior concavity or curvature 45 is provided to conform to the widening of the superior spinous process 138 in an anterior direction toward the superior lamina 148 going in the anterior direction. In general, the superior arm 14 is shaped to conform to anatomy in the location in which it is seated. Likewise, as mentioned above, the shape of the inferior arm 16 is such that an inferior convexity or curvature 47 is provided to conform to the widening of the inferior spinous process 140 in an anterior direction toward the inferior lamina 150. The supraspinous ligament 152 is also shown in FIG. 20.

Any of the spacers disclosed herein are configured for implantation employing minimally invasive techniques including through a small percutaneous incision and may or may not be through the supraspinous ligament. Implantation through the supraspinous ligament involves selective dissection of the supraspinous ligament in which the fibers of the ligament are separated or spread apart from each other in a manner to maintain as much of the ligament intact as possible. This approach avoids crosswise dissection or cutting of the ligament and thereby reduces the healing time and minimizes the amount of instability to the affected spinal segment. While this approach is ideally suited to be performed through a posterior or midline incision, the approach may also be performed through one or more incisions made laterally of the spine with or without affect to the supraspinous ligament. Of course, the spacer may also be implanted in a lateral approach that circumvents the supraspinous ligament altogether.

Other variations and features of the various mechanical spacers are covered by the present invention. For example, a spacer may include only a single arm which is configured to receive either the superior spinous process or the inferior spinous process. The surface of the spacer body opposite the side of the single arm may be contoured or otherwise configured to engage the opposing spinous process wherein the spacer is sized to be securely positioned in the interspinous space and provide the desired distraction of the spinous processes defining such space. The additional extension of the arms) subsequent to their initial deployment in order to seat or to effect the desired distraction between the vertebrae may be accomplished by expanding the body portion of the device instead of or in addition to extending the individual extension members 14, 16. In another variation, the spacer is configured such that arms are bifurcated side-to-side, instead of top-to-bottom for independent lateral deployment. For example in such a variation, the spacer includes a left arm and a right arm, instead of a superior arm and an inferior arm. The right arm includes extensions 42*a* and 44*a* and the left arm includes extensions 42*b* and 44*b* wherein extensions 42*a* and 44*b* are deployed independently of extension 42*b*, 44*b* on the other side of the spacer. This variation allows for the spacer to be inserted in the same manner as described above and one arm is deployed on one side of the both the superior and inferior spinous processes and the second arm is subsequently deployed on the other side of both the superior and inferior spinous processes.

The extension arms of the subject device may be configured to be selectively movable subsequent to implantation, either to a fixed position prior to closure of the access site or otherwise enabled or allowed to move in response to normal spinal motion exerted on the device after deployment. The deployment angles of the extension arms may range from less than 90 degrees (relative to the longitudinal axis defined by the device body) or may extend beyond 90 degrees. Each extension member may be rotationally movable within a range that is different from that of the other extension members. Additionally, the individual superior and/or inferior extensions 42*a*, 42*b*, 44*a*, 44*b* may be movable in any direction relative to the strut or bridge extending between an arm pair or relative to the device body in order to provide shock absorption and/or function as a motion limiter, or serve as a lateral adjustment particularly during lateral bending and axial rotation of the spine. The manner of attachment or affixation of the extensions to the arms may be selected so as to provide movement of the extensions that is passive or active or both. In one variation, the saddle or distance between extensions 42*a* and 42*b* or between 44*a* and 44*b* can be made wider to assist in seating the spinous process and then narrowed to secure the spinous process positioned between extensions 42*a* and 42*b* or between 44*a* and 44*b*.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. An implantable interspinous spacer for engaging adjacent spinous processes of a subject, the implantable interspinous spacer comprising:
    a body defining a passageway;
    arms connected to the body, each arm having a pair of extensions spaced apart from one another to define an opening, wherein the arms are rotatable with respect to the body such that the arms move from an undeployed configuration for inserting the implantable interspinous spacer between the spinous processes to a first deployed configuration for positioning each spinous process within one of the openings between the extensions, and wherein the arms are linearly movable with respect to the body such that the arms move from the first deployed configuration to a second deployed configuration for distracting the spinous processes; and
    an actuator assembly configured to deploy the arms and comprising an actuator, wherein the actuator is movable along the passageway to rotate the arms from the undeployed configuration to the first deployed configuration and to linearly move the arms from the first deployed configuration to the second deployed configuration.

2. The implantable interspinous spacer of claim 1 wherein the actuator includes a proximal end, a distal end, at least one bearing surface at the distal end, wherein the at least one bearing surface is configured to engage caroming surfaces of the arms when the actuator moves along the passageway to cause the arms to roll along the at least one bearing surface such that the arms move from the undeployed configuration toward the first deployed configuration, and wherein each arm has a substantially flat surface for contacting the at least one bearing surface when the arms are in the first deployed configuration.

3. The implantable interspinous spacer of claim 1 wherein the arms in the undeployed configuration are substantially parallel to a longitudinal axis of the body, and wherein the arms in the first deployed configuration are substantially perpendicular to the longitudinal axis of the body.

4. The implantable interspinous spacer of claim 1 wherein the actuator is movable along the passageway to cause the arms to rotate from the undeployed configuration to the first deployed configuration, and the actuator is further movable along the passageway to push the arms away from each other toward the second deployed configuration.

5. The implantable interspinous spacer of claim 1 wherein at least one of the arms includes
    a first pin positioned in a first slot in the body and defining an axis of rotation about which the at least one arm rotates to move from the undeployed configuration to the first deployed configuration, and
    a second pin positioned in a second slot in the body and movable along the second slot to move the arm from the undeployed configuration and the second deployed configuration.

6. The implantable interspinous spacer of claim 1 wherein each arm rotates approximately 90 degrees when that arm moves from the undeployed configuration to the first deployed configuration.

7. The implantable interspinous spacer of claim 1 wherein each arm is configured to rotate outwardly into a planar space that is substantially transverse to a longitudinal axis of the body, and wherein each arm is configured to translate in the planar space away from the longitudinal axis when the arm moves from the first deployed configuration toward the second deployed configuration.

8. The implantable interspinous spacer of claim 1 wherein the actuator includes two bearing surfaces that converge towards a distal end of the actuator, and wherein each bearing surface is positioned to contact and move one of the arms.

9. The implantable interspinous spacer of claim 1 wherein a proximal end of the actuator assembly is configured for attachment to an instrument capable of causing movement of actuator with respect to the body.

10. The implantable interspinous spacer of claim 1 wherein each of the openings is configured to receive one of the spinous processes such that the extensions are located on opposite sides of the spinous process.

11. The implantable interspinous spacer of claim 1 wherein the actuator is linearly movable along the passageway so as to push the arms away from one another to translate the arms outwardly a sufficient distance to distract the spinous processes.

12. The implantable interspinous spacer of claim 1 wherein the actuator assembly is configured to begin linearly moving the arms after the arms have rotated from the undeployed configuration to the deployed configuration.

13. The implantable interspinous spacer of claim 1 wherein the arms include a first arm and a second arm, wherein the first arm is linearly movable in a first direction when the first arm moves toward the second deployed configuration, and wherein the second arm is linearly movable in a second direction generally opposite the first direction when the second arm moves toward the second deployed configuration.

14. An implantable spacer for distracting adjacent spinous processes of a subject, the implantable spacer comprising:
a spacer body defining a passageway;
arms coupled to the spacer body and each arm including
a pair of extensions spaced apart from one another to define an opening between the extensions; and
an actuator assembly in the passageway and operable to cause the arms to rotate from an undeployed configuration for delivering the implantable spacer between the spinous processes toward a deployed configuration for positioning spinous processes in the openings, and wherein the actuator assembly is operable to translate the arms relative to the spacer body such that the arms move linearly from the deployed configuration to a distracted configuration for distracting the spinous processes positioned in the openings.

15. The implantable spacer of claim 14 wherein the actuator assembly includes an actuator with a tapered head, and wherein the actuator is linearly movable along the passageway to cause the arms to roll along the tapered head as the arms rotate from the undeployed configuration to the deployed configuration.

16. The implantable spacer of claim 14 wherein the arms have camming surfaces and locking surfaces, wherein the camming surfaces roll along a tapered head of the actuator assembly when the tapered head moves linearly along the passageway and the arms move toward the deployed configuration, and wherein the locking surfaces engage the tapered head when the arms are in the distracted configuration.

17. The implantable spacer of claim 14 wherein the arms in the undeployed configuration are substantially parallel to a longitudinal axis of the spacer body, and wherein the arms in the deployed configuration are substantially perpendicular to the longitudinal axis of the spacer body.

18. The implantable spacer of claim 14 wherein the arms include a first arm and a second arm, wherein the first arm includes
a first pin positioned in a first slot in the spacer body and about which the extensions of the first arm rotate when the first arm moves from the undeployed configuration toward the deployed configuration, and
a second pin positioned in a second slot in the spacer body and movable along the second slot to move the first arm toward the deployed configuration.

19. The implantable spacer of claim 14 wherein the actuator assembly is connected to the spacer body and is configured to mechanically drive the arms from the undeployed configuration to the distracted configuration in response to operation of the actuator assembly.

20. The implantable spacer of claim 14 wherein the arms are U-shaped.

21. The implantable spacer of claim 14 wherein each of the openings is configured to receive one of the spinous processes such that the extensions are located on opposite sides of the spinous process.

22. The implantable spacer of claim 14 wherein the actuator assembly has a linearly movable actuator configured to push the arms away from one another to translate the arms a sufficient distance to distract the spinous processes when the actuator moves through the passageway.

23. The implantable spacer of claim 14 wherein the actuator assembly is configured to begin translating the arms after the arms have rotated from the undeployed configuration to the deployed configuration.

24. The implantable spacer of claim 14 wherein the actuator assembly is configured to begin linearly moving the arms after the arms have rotated from the undeployed configuration to the deployed configuration.

25. An implantable spacer for distracting adjacent spinous processes of a subject, the implantable spacer comprising:
a spacer body defining a passageway;
arms coupled to the spacer body and each arm including
a pair of extensions spaced apart from one another to define an opening between the extensions, wherein the arms include a first arm and a second arm, wherein the first arm includes
a first pin positioned in a first slot in the spacer body and about which the extensions of the first arm rotate when the first arm moves from the undeployed configuration toward the deployed configuration, and
a second pin positioned in a second slot in the spacer body and movable along the second slot to move the first arm toward the deployed configuration, wherein the second slot has an arcuate section and a linear section, wherein the second pin moves along the arcuate section when the first arm rotates toward the deployed configuration, and wherein the second pin moves along the linear section when the first arm moves toward the distracted configuration; and
an actuator assembly in the passageway and operable to cause the arms to rotate from an undeployed configuration for delivering the implantable spacer between the spinous processes toward a deployed configuration for positioning spinous processes in the openings, and wherein the actuator assembly is operable to drive the arms from the deployed configuration to a distracted configuration for distracting the spinous processes positioned in the openings.

26. The implantable spacer of claim 25 wherein the actuator assembly pushes the first and second arms away from each other when the first and second arms move toward the distracted configuration.

27. An implantable interspinous spacer for engaging adjacent first and second vertebrae of a subject, comprising:
   a body;
   first and second arms each rotatable with respect to the body to move from a delivery configuration to a rotated configuration for engaging the first and second vertebrae, and wherein the first and second arms are linearly movable with respect to the body to move from the rotated configuration to a distraction configuration; and
   an actuator movable along the body to rotate the first and second arms toward the rotated configuration and to linearly move the first and second arms toward the distracted configuration.

28. The implantable interspinous spacer of claim 27, wherein the actuator moves linearly along a passage in the body to drive the first and second arms away from the delivery configuration.

\* \* \* \* \*